United States Patent
Uesugi et al.

(10) Patent No.: US 9,335,323 B2
(45) Date of Patent: May 10, 2016

(54) METHOD FOR SORTING OF PLURIPOTENT CELLS

(71) Applicant: KYOTO UNIVERSITY, Kyoto (JP)

(72) Inventors: Motonari Uesugi, Kyoto (JP); Nao Hirata, Kyoto (JP); Asako Murata, Kyoto (JP); Young-Tae Chang, Kyoto (JP); Norio Nakatsuji, Kyoto (JP); Hirofumi Suemori, Kyoto (JP); Eihachiro Kawase, Kyoto (JP); Kaori Yamauchi, Kyoto (JP); Kazumitsu Ueda, Kyoto (JP); Yuto Fujibayashi, Kyoto (JP); Shinya Yamanaka, Kyoto (JP); Masato Nakagawa, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/370,331

(22) PCT Filed: Jan. 7, 2013

(86) PCT No.: PCT/JP2013/050501
§ 371 (c)(1),
(2) Date: Jul. 2, 2014

(87) PCT Pub. No.: WO2013/103156
PCT Pub. Date: Jul. 11, 2013

(65) Prior Publication Data
US 2015/0031062 A1 Jan. 29, 2015

Related U.S. Application Data

(60) Provisional application No. 61/584,110, filed on Jan. 6, 2012.

(51) Int. Cl.
| | |
|---|---|
| A61K 51/04 | (2006.01) |
| G01N 21/64 | (2006.01) |
| C12Q 1/00 | (2006.01) |
| G01N 33/50 | (2006.01) |
| C12N 5/0735 | (2010.01) |
| C12N 5/074 | (2010.01) |
| C09B 11/24 | (2006.01) |
| C09B 11/28 | (2006.01) |
| C09B 15/00 | (2006.01) |
| C09B 69/10 | (2006.01) |

(52) U.S. Cl.
CPC ............ *G01N 33/5073* (2013.01); *C09B 11/24* (2013.01); *C09B 11/28* (2013.01); *C09B 15/00* (2013.01); *C09B 69/109* (2013.01); *C12N 5/0606* (2013.01); *C12N 5/0696* (2013.01); *G01N 2333/70596* (2013.01); *G01N 2333/914* (2013.01)

(58) Field of Classification Search
None
See application file for complete search history.

(56) References Cited

U.S. PATENT DOCUMENTS

2009/0227467 A1  9/2009 Chang et al.

OTHER PUBLICATIONS

Kim et al, The Multidrug Resistance Transporter ABCG2 (Breast Cancer Resistance Protein 1) Effluxes Hoechst 33342 and Is Overexpressed in Hematopoietic Stem Cells, Clinical Cancer Research, vol. 8, Jan. 22-28, 2002.*
Ahn et al., "Combinatorial Rosamine Library and Application to in Vivo Glutathione Probe," *J. Am. Chem. Soc.*, vol. 129(15), pp. 4510-4511 (2007).
Hattori et al., "Nongenetic method for purifying stem cell-derived cardiomyocytes," *Nat. Methods*, vol. 7(1), pp. 61-66 (Jan. 2010).
Henderson et al., "Preimplantation Human Embryos and Embryonic Stem Cells Show Comparable Expression of Stage-Specific Embryonic Antigens," *Stem Cells*, vol. 20, pp. 329-337 (2002).
Mitsui et al., "The Homeoprotein Nanog Is Required for Maintenance of Pluripotency in Mouse Epiblast and ES Cells," *Cell*, vol. 113, pp. 631-642 (May 30, 2003).
Orlic et al., "Purification and Characterization of Heterogeneous Pluripotent Hematopoietic Stem Cell Populations Expressing High Levels of c-kit Receptor," *Blood*, vol. 82(3), pp. 762-770 (Aug. 1, 1993).
Rosner et al., "A POU-domain transcription factor in early stem cells and germ cells of the mammalian embryo," *Nature*, vol. 345, pp. 686-692 (Jun. 21, 1990).
Shevinsky et al., "Monoclonal Antibody to Murine Embryos Defines a Stage-Specific Embryonic Antigen Expressed on Mouse Embryos and Human Teratocarcinoma Cells," *Cell*, vol. 30, pp. 697-705 (Oct. 1982).
Takahashi et al., "Induction of Pluripotent Stem Cells from Adult Human Fibroblasts by Defined Factors," *Cell*, vol. 131, pp. 861-872 (Nov. 30, 2007).
Thomson et al., "Isolation of a primate embryonic stem cell line," *Proc. Natl. Acad. Sci. USA*, vol. 92, pp. 7844-7848 (Aug. 1995).
Thomson et al., "Embryonic Stem Cell Lines Derived from Human Blastocysts," *Science*, vol. 282, pp. 1145-1147 (Nov. 6, 1998).

* cited by examiner

*Primary Examiner* — Maria Marvich
(74) *Attorney, Agent, or Firm* — Knobbe, Martens, Olson & Bear, LLP

(57) ABSTRACT

A method for sorting pluripotent cells using a compound which is eliminated from the pluripotent cells through the MDR1 transporter.

10 Claims, 7 Drawing Sheets

METHOD FOR SORTING OF PLURIPOTENT CELLS

This application is the U.S. National Phase under 35 U.S.C. §371 of International Application No. PCT/JP2013/050501, filed Jan. 7, 2013, designating the U.S., and published in English as WO 2013/103156 on Jul. 11, 2013, which claims priority to U.S. Provisional Application No. 61/584,110, filed Jan. 6, 2012, the entire contents of which are incorporated herein by reference.

FIELD OF INVENTION

The present invention relates to a method of sorting pluripotent cells from sample cells such as those which contain pluripotent cells and differentiated cells. The present invention also relates to a method of selecting pluripotent cells and a method of selecting differentiated cells.

BACKGROUND ART

Human embryonic stem (ES) cells (Thomson, J. A. et al. *Science* 1998, 282, 1145-1147) and induced pluripotent stem (iPS) cells (Takahashi, K. et al. *Cell* 2007, 131, 861-872), which proliferate infinitely and differentiate into numerous cell types, have been serving as valuable tools for basic biological research and as promising resources for regeneration therapy. Despite advances, substantial challenges remain for clinical application of stem cells. One safety concern has been posed by the appearance of a teratoma in animal models transplanted with cell samples containing a small amount of undifferentiated stem cells. Strategies to detect and ablate undifferentiated stem cells are required for safer stem cell therapy.

For the detection of human pluripotent stem cells, antibodies against SSEA-4 (stage-specific embryonic antigen 4) have extensively been used (Shevinsky, L. H. et al. *Cell* 1982, 30, 697-705). SSEA-4 is a glycolipid that is expressed on the cell surface of early embryos and presented selectively on the surface of human ES and EC (embryonic carcinoma) cells by unknown reasons (Henderson, J. K. et al. *Stem Cells* 2002, 20, 329-337). Other markers of human stem cells include Oct3/4 and Nanog, transcription factors required for the maintenance of undifferentiated states of stem cells and downregulated upon differentiation (Rosner, M. H. et al. *Nature* 1990, 345, 686-692, and Mitsui, K. et al. *Cell* 2003, 113, 631-642). Although their antibodies are highly useful in detecting pluripotent cells, these unstable protein tools suffer from their high cost and careful procedures including fixation and permealization of cells. Another routine marker of human stem cells is alkaline phosphatase (Thomson, J. A. et al. *Proc. Natl. Acad. Sci. USA* 1995, 92, 7844-7848). Although the assay for its enzymatic activity represents a simple and highly useful method for detecting stem cells, a major concern is its specificity to pluripotent stem cells because this house-keeping enzyme is expressed widely in a number of other cell types.

SUMMARY OF INVENTION

In order to sorting pluripotent stem cells with high specificity, the inventors of the present invention assiduously studied and found that pluripotent cells can be sorted by using a compound which is eliminated from the pluripotent cells through MDR1 transporter, thereby completed the present invention.

The present invention has the following features.

[1] A method of sorting pluripotent cells comprising the following steps;

(i) contacting sample cells and a compound which is eliminated from the pluripotent cells through MDR1 transporter, and (ii) detecting the cells which have accumulated the compound as pluripotent cells.

[2] The method of [1], wherein the compound has a structure of the formula (I):

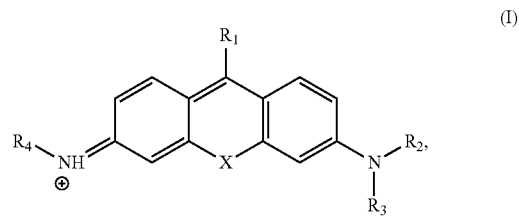

wherein $R_1$ is selected from the group consisting of the formula (II), (III) and (IV):

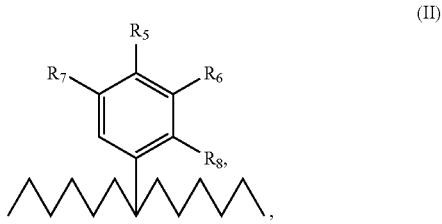

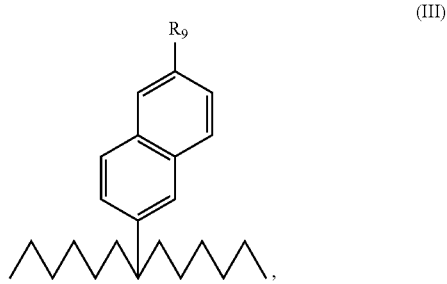

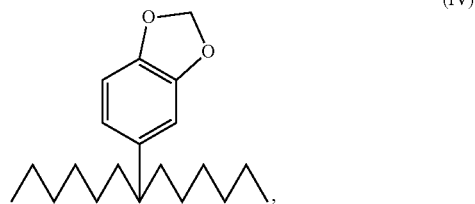

where $R_5$, $R_6$, $R_7$, $R_8$ and $R_9$ are respectively selected from the group consisting of hydrogen, halogen, C1 to C6 alkyl, phenyl, $-OR_{10}$ and $-SR_{10}$ where $R_{10}$ is C1 to C6 alkyl or aryl, wherein $R_2$, $R_3$ and $R_4$ are respectively selected from the group consisting of hydrogen, C1 to C6 alkyl, $-(CH_2)_m NR_{11}R_{12}$ where m is an integer of 1 to 12 and, $R_{11}$ and $R_{12}$ are respectively selected from the group consisting of hydrogen, C1 to C6 alkyl and chloroacetyl, or $R_2$ and $R_3$ form the cyclic conformation of the formula (V) together with the nitrogen atom to which $R_2$ and $R_3$ are bound:

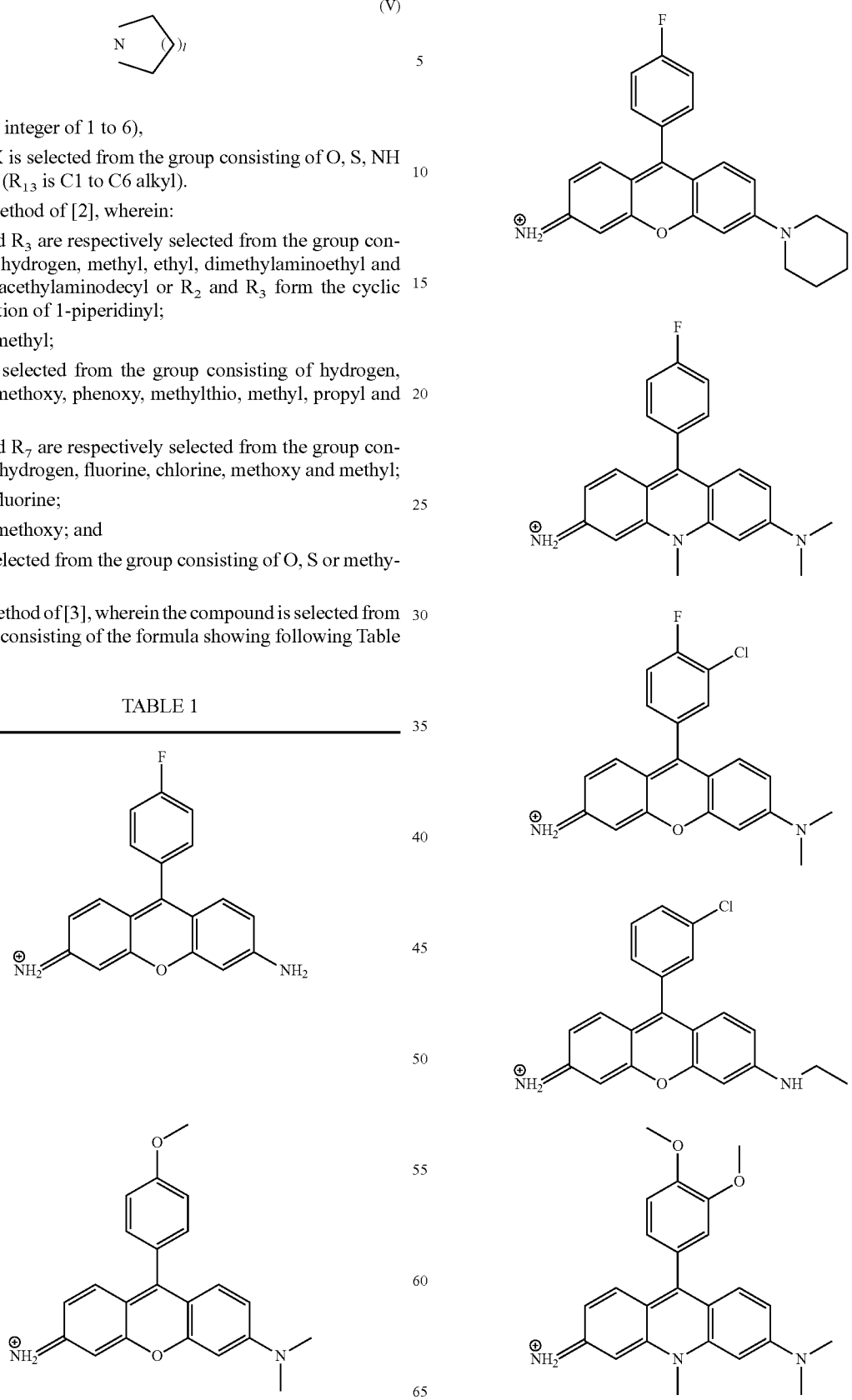

(l is an integer of 1 to 6),
wherein X is selected from the group consisting of O, S, NH and $NR_{13}$ ($R_{13}$ is C1 to C6 alkyl).

[3] The method of [2], wherein:

the $R_2$ and $R_3$ are respectively selected from the group consisting of hydrogen, methyl, ethyl, dimethylaminoethyl and 10-chloroacethylaminodecyl or $R_2$ and $R_3$ form the cyclic conformation of 1-piperidinyl;

the $R_4$ is methyl;

the $R_5$ is selected from the group consisting of hydrogen, fluorine, methoxy, phenoxy, methylthio, methyl, propyl and phenyl;

the $R_6$ and $R_7$ are respectively selected from the group consisting of hydrogen, fluorine, chlorine, methoxy and methyl;

the $R_8$ is fluorine;

the $R_9$ is methoxy; and the X is selected from the group consisting of O, S or methylamino.

[4] The method of [3], wherein the compound is selected from the group consisting of the formula showing following Table 1:

TABLE 1

TABLE 1-continued
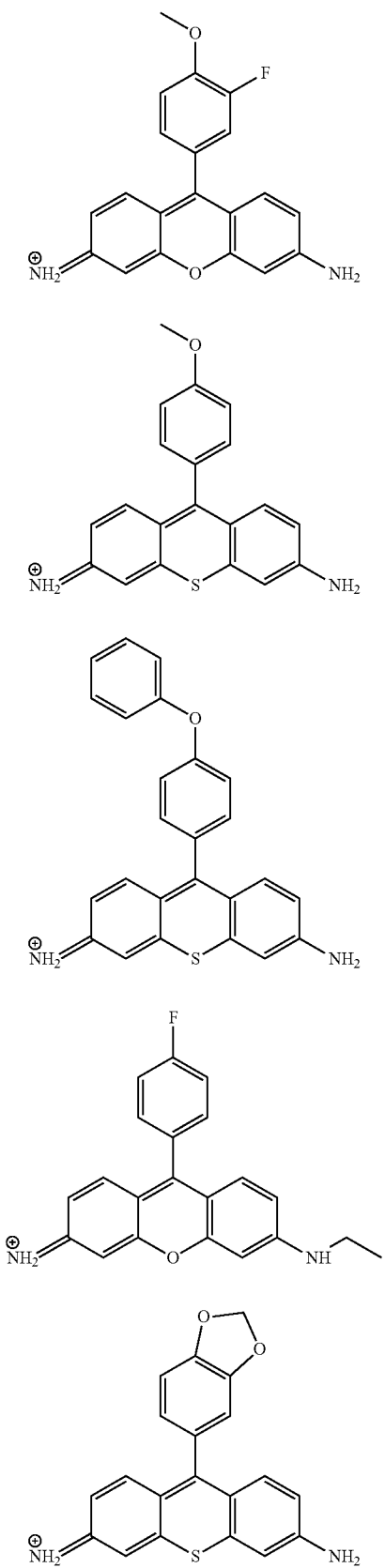
TABLE 1-continued
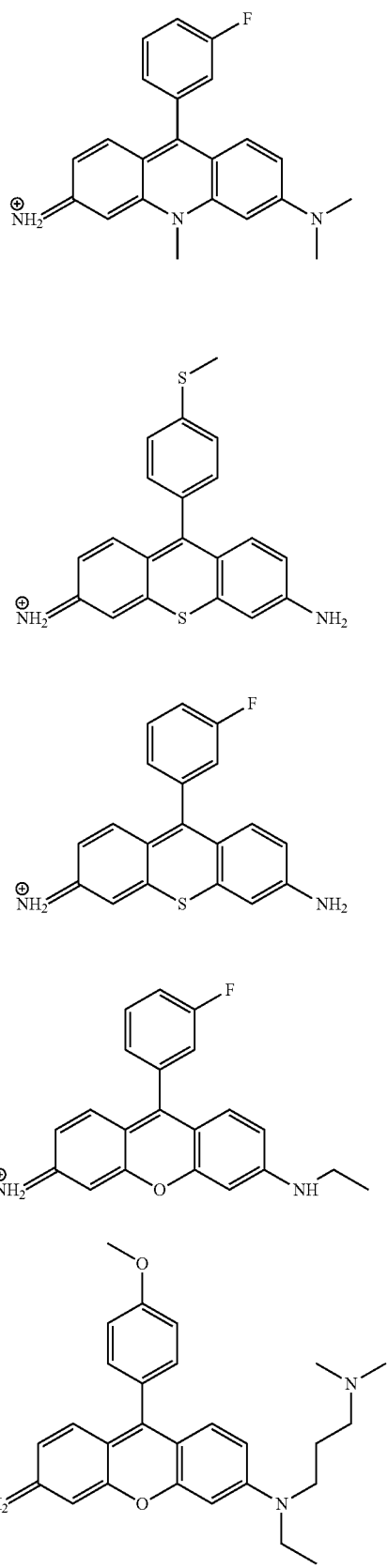

TABLE 1-continued
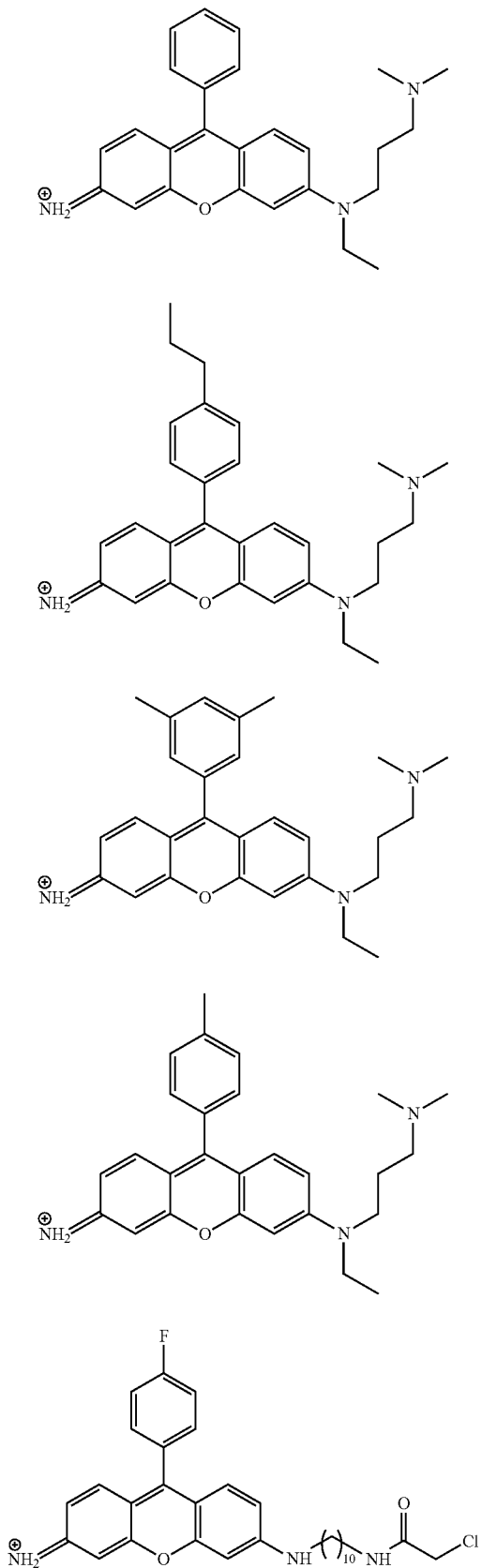
TABLE 1-continued
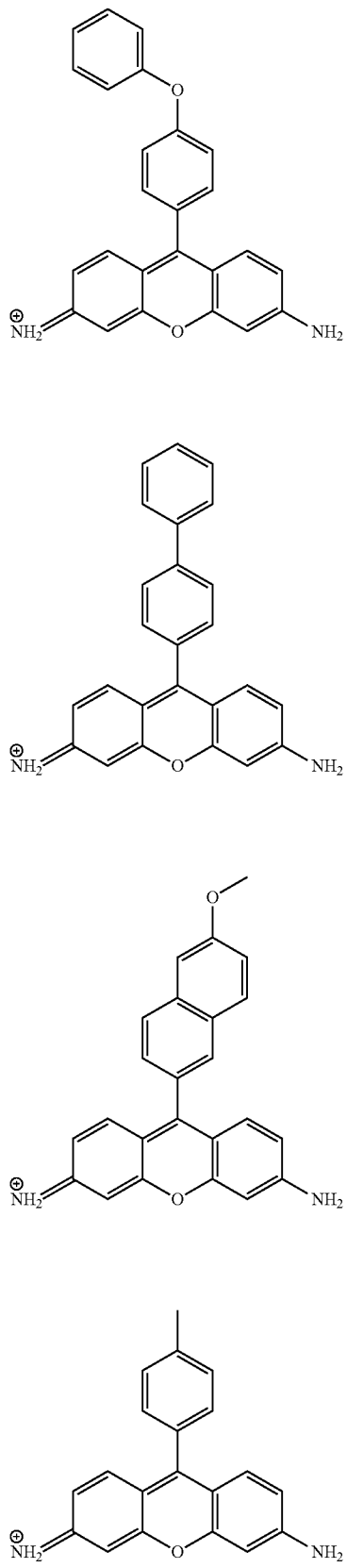

TABLE 1-continued

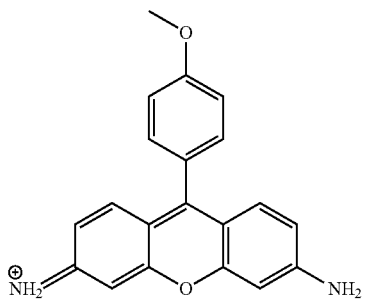

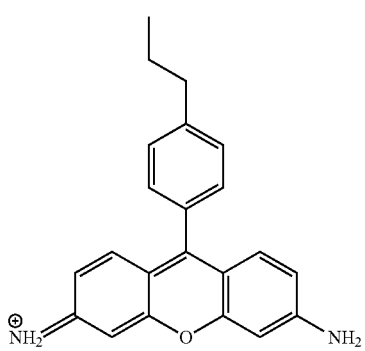

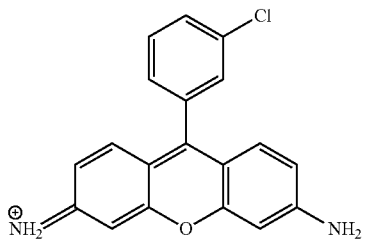 [SMILES: Nc1ccc2c(-c3cccc(Cl)c3)c3ccc(=[NH2+])cc-3oc2c1]

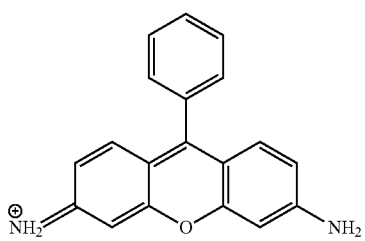

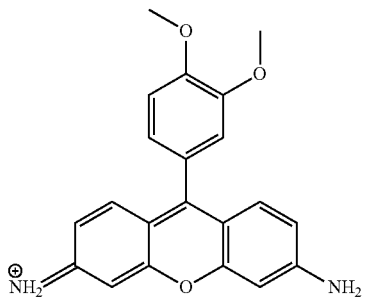

TABLE 1-continued

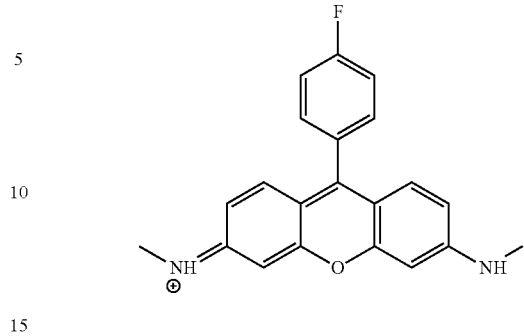

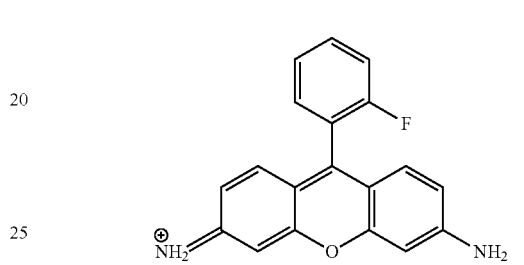

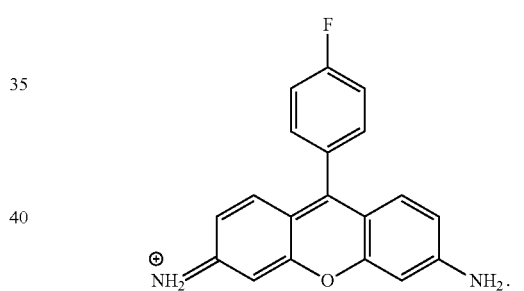

[5] The method of [4], wherein the compound is the following formula

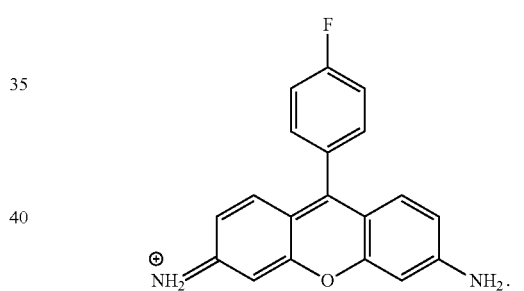

[6] The method of [1], wherein the sample cells are somatic cells introduced with a reprogramming factor.

[7] The method of [6], wherein the reprogramming factor is at least one factor selected from the group consisting of Oct family gene or gene product thereof, Sox family gene or gene product thereof, Klf4 family gene or gene product thereof and Myc family gene or gene product thereof.

[8] The method of [1], wherein the sample cells consist of pluripotent cells induced to differentiate to somatic cells.

[9] A method of selecting pluripotent cells comprising the step of sorting pluripotent cells by the method of [1] and selecting the sorted cells.

[10] A method of selecting differentiated cells, comprising the step of sorting pluripotent cells by the method of claim 1 and excluding the sorted cells from the sample cells.

[11] A kit for sorting pluripotent cell comprising a compound which is eliminated from the pluripotent cells through MDR1 transporter.

[12] The kit of [11], wherein the compound has a structure of the formula (I):

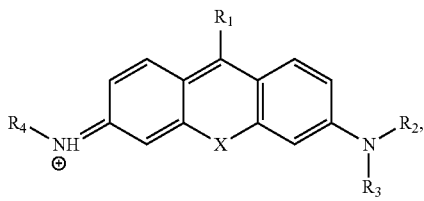

wherein R₁ is selected from the group consisting of the formula (II), (III) and (IV):

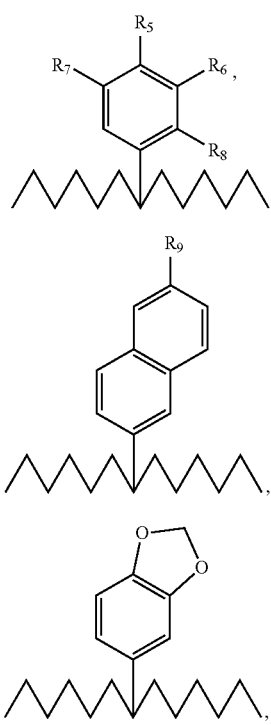

(1 is an integer of 1 to 6),
wherein X is selected from the group consisting of O, S, NH and NR₁₃ (R₁₃ is C1 to C6 alkyl).

[13] The kit of [12], wherein:
the R₂ and R₃ are respectively selected from the group consisting of hydrogen, methyl, ethyl, dimethylaminoethyl and 10-chloroacethylaminodecyl or R₂ and R₃ form the cyclic conformation of 1-piperidinyl;
the R₄ is methyl;
the R₅ is selected from the group consisting of hydrogen, fluorine, methoxy, phenoxy, methylthio, methyl, propyl and phenyl;
the R₆ and R₇ are respectively selected from the group consisting of hydrogen, fluorine, chlorine, methoxy and methyl;
the R₈ is fluorine;
the R₉ is methoxy; and
the X is selected from the group consisting of O, S or methylamino.

[14] The kit of [13], wherein the compound is selected from the group consisting of the formula shown in Table 1.

[15] The kit of [14], wherein the compound is the following formula

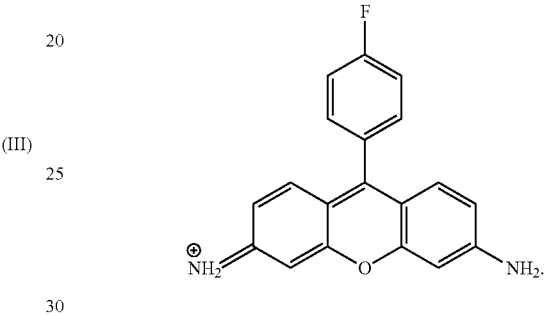

BRIEF DESCRIPTION OF DRAWINGS

FIG. 1, panels B-D show flow cytometry dot-plot images of human iPS cells and feeder cells stained by Compound 1 (2 μM) for 3 hours (B); human iPS cells and feeder cells stained with a fluorescence-labeled anti-SSEA-4 antibody (α-SSEA-4-Alexa647) (C); and doubly-stained human iPS cells and feeder cells with Compound 1 and α-SSEA-4-Alexa647 (D).

FIG. 3, panels e and f (photographs) show bright-field image (e) and fluorescence microscopic image (f) of human iPS cells stained with Compound 1 (1 μM) for 2 hours in the presence of CCCP (5 μM). Scale bar: 150 μm.

FIG. 4, panel b shows graph of fold increase of ABCB1 (MDR1), ABCC1 (MRP1), and ABCG2 (BCRP) transporter in human ES cells (open bar) and differentiated cells (shaded bar). Each bar consists of five hES cell lines (KhES-1, KhES-2, KhES-3, KhES-4, KhES-5). FIG. 4, panels c and d (photographs) show fluorescence microscopic images of KB3-1, a cell line with no MDR1 expression (c) and MDR1-expressing model cell line (KB/MDR1) (d) stained with Compound 1. Scale bar: 2 μm.

FIG. 5, panels c-e show flow-cytometric histograms for human ES cells and differentiated cells incubated with Compound 1 (c), human ES cells and differentiated cells treated with AlexaFluor647-labelled anti-MDR1 antibody (d), and human ES cells and differentiated cells incubated with Compound 1 after treatment with cyclosporine A (CsA) (e).

FIG. 6, panel b shows fluorescence histograms from flow cytometric analysis on human iPS cells and cardiomyocytes derived from the iPS cells, which stained with KP-1 (shown as KP-1 (+)) or not (shown as KP-1(−)).

FIG. 7, panel b (photograph) shows KP-1 efflux by ABCC5-expressing cells. The expression vector of GFP-fused ABCC5 was transfected into HEK293 cells. The HEK293 and ABCC5-expressing HEK293 treated with KP-1 (shown as KP-1(+)) or not (shown as KP-1(−)) were observed with 555-nm short-pass emission filter for observation both of GFP and KP-1 and 560 long-pass emission filters for observation of only KP-1.

DETAILED DESCRIPTION OF THE INVENTION

Figure 1:
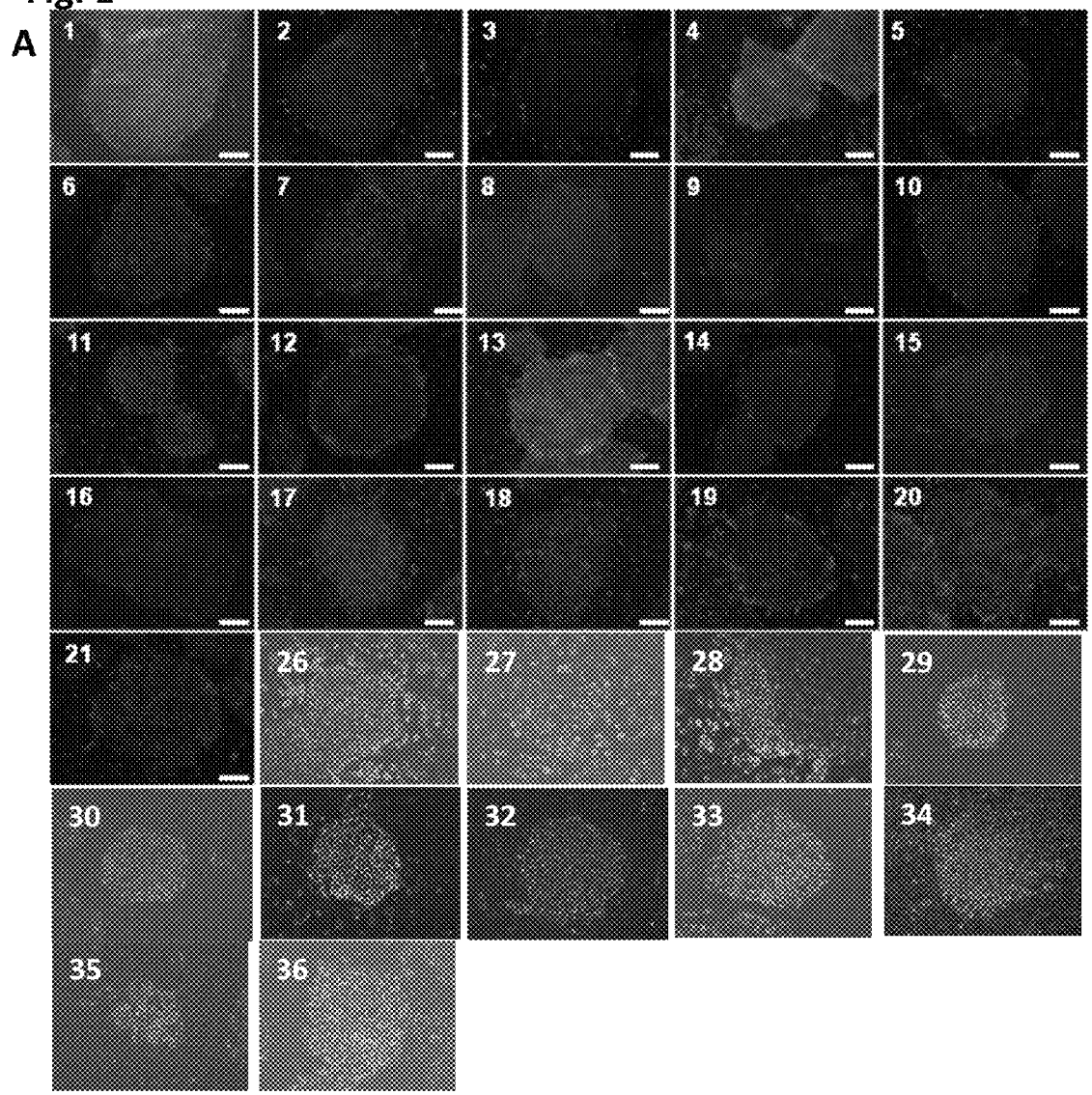
FIG. 1, panel A shows fluorescence images (photographs) of human iPS cells treated with each compound (1-21 and 26-36). Scale bar: 300 μm.
Figure 1:
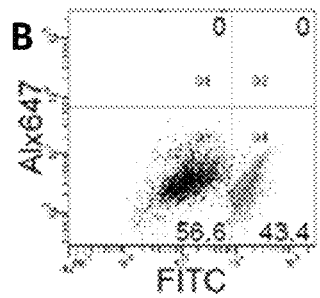
Figure 1:
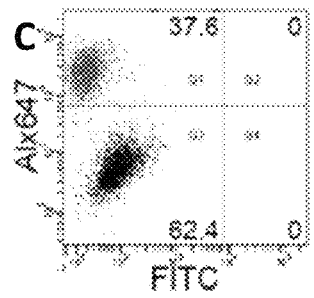
Figure 1:
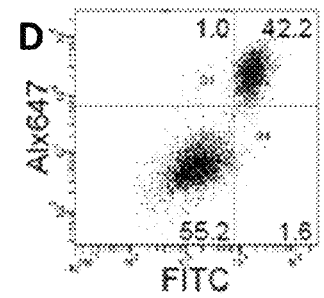

The present invention provides a method of sorting pluripotent cells comprising the following steps;
(i) contacting sample cells and a compound which is eliminated from the pluripotent cells through MDR1 transporter, and
(ii) detecting the cells which have accumulated the compound as pluripotent cells.

The nucleotide sequence information of the MDR1 transporter and the amino acid sequence information of proteins encoded by the MDR1 cDNA can be obtained by referring to NCBI accession number: NM_000927.

The compound which is eliminated from the pluripotent cells through MDR1 transporter can be recognized by using the cells with or without MDR1 as described in Example 5.

In one embodiment of the present invention, the compound, which is eliminated from the pluripotent cells through MDR1 transporter, has formula (I):

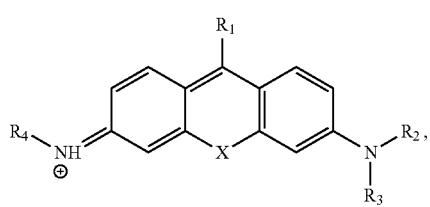

wherein
$R_1$ is selected from the group consisting of the formula (II), (III) and (IV):

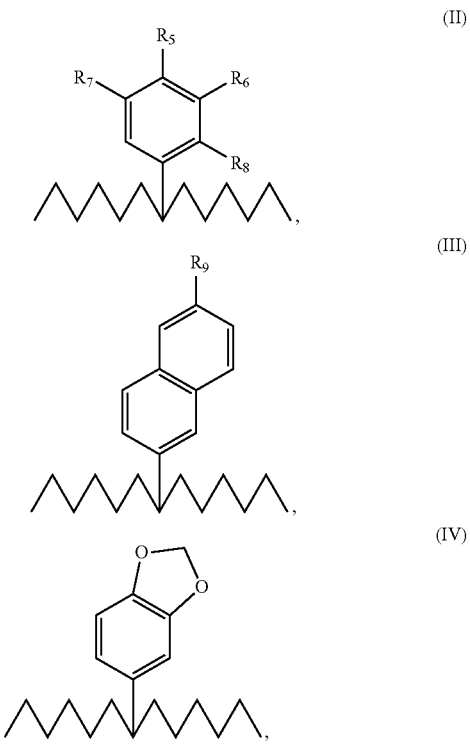

($R_5$, $R_6$, $R_7$, $R_8$ and $R_9$ are respectively selected from the group consisting of hydrogen, halogen, C1 to C6 alkyl, phenyl, —$OR_{10}$ and —$SR_{10}$ where $R_{10}$ is C1 to C6 alkyl or aryl, preferably the $R_5$ is selected from the group consisting of hydrogen, fluorine, methoxy, phenoxy, methylthio, methyl, propyl and phenyl, the $R_6$ and $R_7$ are respectively selected from the group consisting of hydrogen, fluorine, chlorine, methoxy and methyl, the $R_8$ is fluorine, and the $R_9$ is methoxy),
wherein
$R_2$, $R_3$ and $R_4$ are respectively selected from the group consisting of hydrogen, C1 to C6 alkyl, —$(CH_2)_m NR_{11}R_{12}$ where m is an integer of 1 to 12 and, $R_{11}$ and $R_{12}$ are respectively selected from the group consisting of hydrogen, C1 to C6 alkyl and chloroacetyl, or $R_2$ and $R_3$ form the cyclic conformation of the formula (III) together with the nitrogen atom to which $R_2$ and $R_3$ are bound:

(l is an integer of 1 to 6),
preferably the $R_2$ and $R_3$ are respectively selected from the group consisting of hydrogen, methyl, ethyl, dimethylaminoethyl and 10-chloroacethylaminodecyl or $R_2$ and $R_3$ form the cyclic conformation of 1-piperidinyl, and the $R_4$ is methyl
wherein
X is selected from the group consisting of O, S, NH and $NR_{13}$ ($R_{13}$ is C1 to C6 alkyl), preferably the X is selected from the group consisting of O, S or methylamino.

In the present invention, the C1 to C6 alkyl means a linear or branched chain saturated hydrocarbon group having a carbon number of 1-6, namely, methyl, ethyl, propyl, isopropyl, n-butyl, sec-butyl, isobutyl, tert-butyl, heptyl, or hexyl.
In one embodiment of the present invention, more preferable compounds are described in the following Table 2.
TABLE 2
| No | Compound structure |
|---|---|
| 1 | 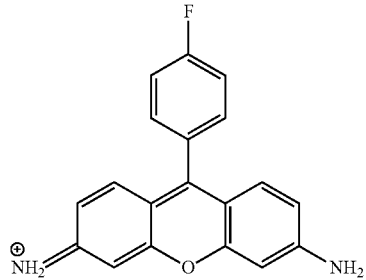 [SMILES: Nc1ccc2c(-c3ccc(F)cc3)c3ccc(=[NH2+])cc-3oc2c1] |
| 2 | |
| 3 | |
| 4 | |
| 5 | 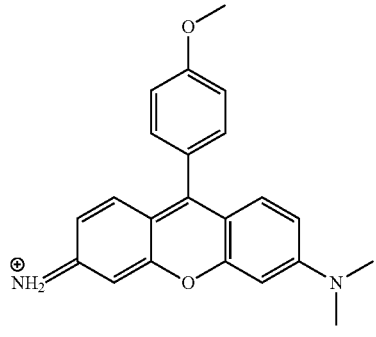 [SMILES: COc1ccc(-c2c3ccc(=[NH2+])cc-3oc3cc(N(C)C)ccc23)cc1] |
| 6 | 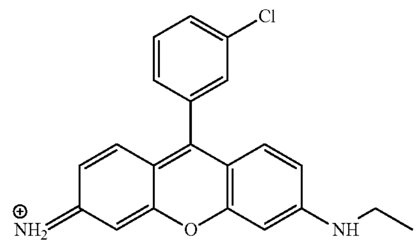 |
| 7 | 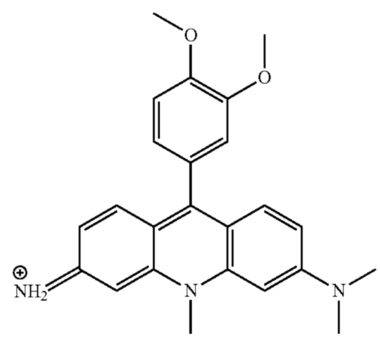 [SMILES: COc1ccc(-c2c3ccc(=[NH2+])cc-3n(C)c3cc(N(C)C)ccc23)cc1OC] |
| 8 | 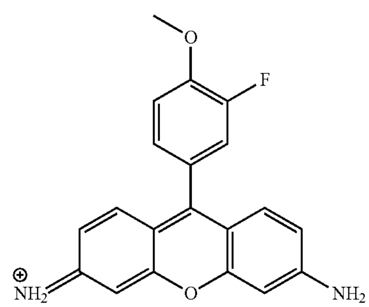 |
| 9 | 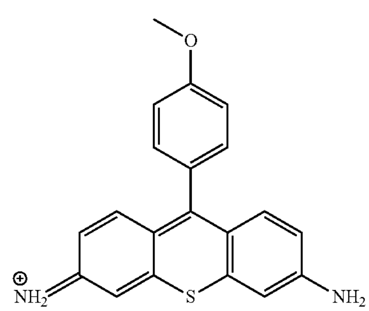 |

TABLE 2-continued
Compounds
| No | Compound structure |
|---|---|
| 10 | 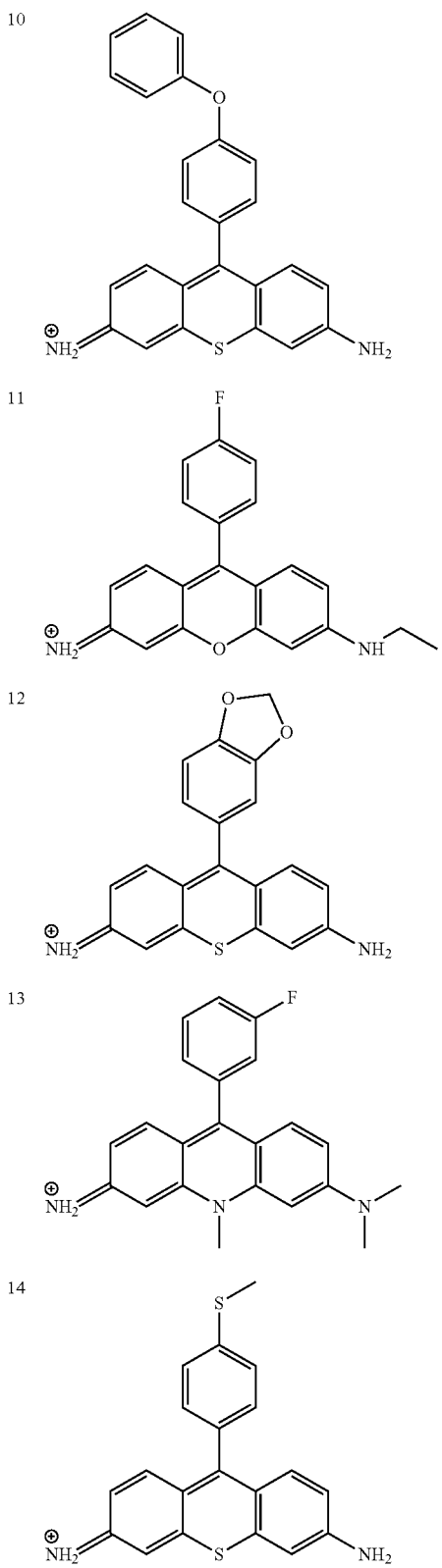 |
| 11 | 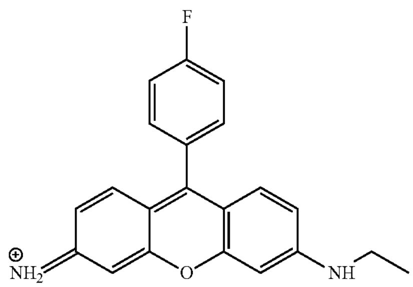 [SMILES: CCNc1ccc2c(-c3ccc(F)cc3)c3ccc(=[NH2+])cc-3oc2c1] |
| 12 | 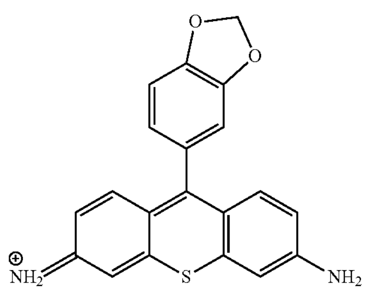 [SMILES: Nc1ccc2c(-c3ccc4c(c3)OCO4)c3ccc(=[NH2+])cc-3sc2c1] |
| 13 | 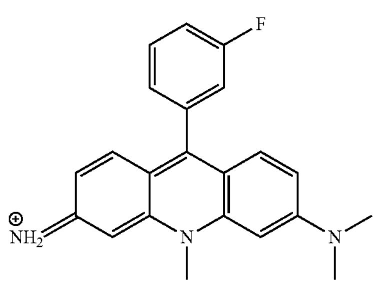 [SMILES: CN(C)c1ccc2c(-c3cccc(F)c3)c3ccc(=[NH2+])cc-3n(C)c2c1] |
| 14 | 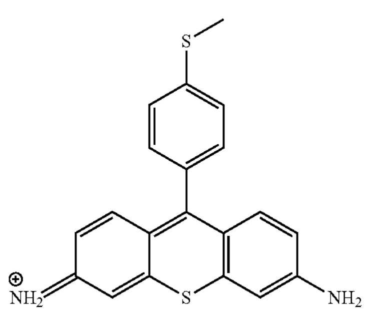 |
| 15 | 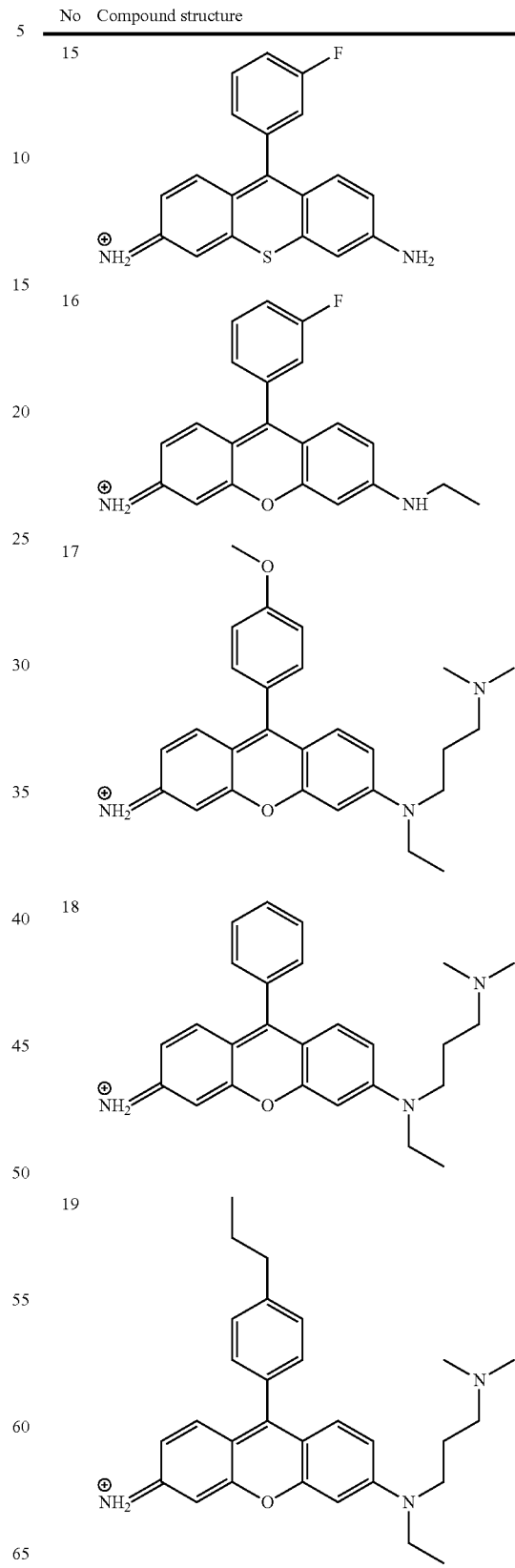 |
| 16 | 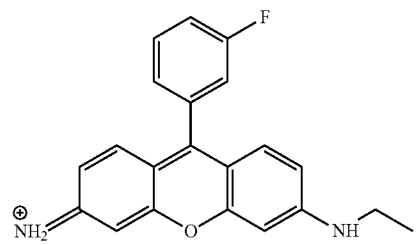 |
| 17 | 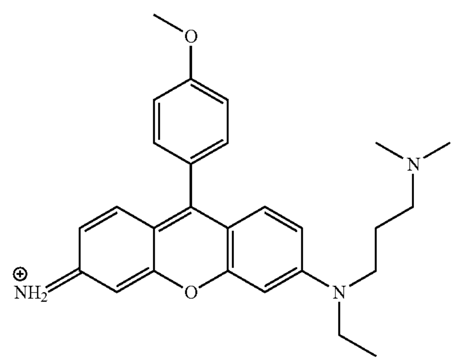 [SMILES: CCN(CCCN(C)C)c1ccc2c(-c3ccc(OC)cc3)c3ccc(=[NH2+])cc-3oc2c1] |
| 18 | 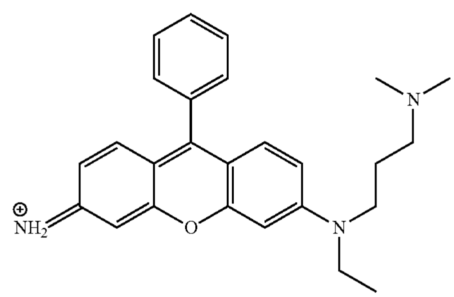 [SMILES: CCN(CCCN(C)C)c1ccc2c(-c3ccccc3)c3ccc(=[NH2+])cc-3oc2c1] |
| 19 | 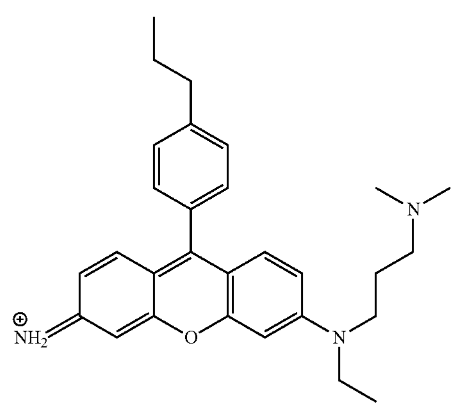 [SMILES: CCCc1ccc(-c2c3ccc(=[NH2+])cc-3oc3cc(N(CC)CCCN(C)C)ccc23)cc1] |

TABLE 2-continued
Compounds
| No | Compound structure |
|---|---|
| 20 | 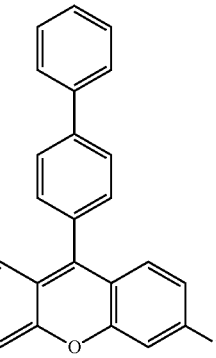 |
| 21 | 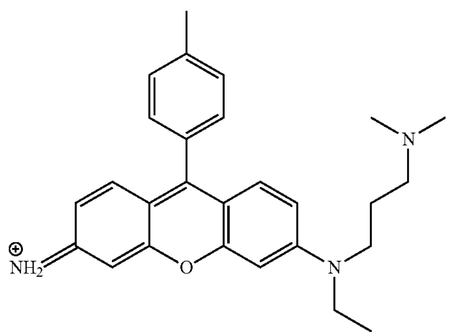 [SMILES: CCN(CCCN(C)C)c1ccc2c(-c3ccc(C)cc3)c3ccc(=[NH2+])cc-3oc2c1] |
| 22 | 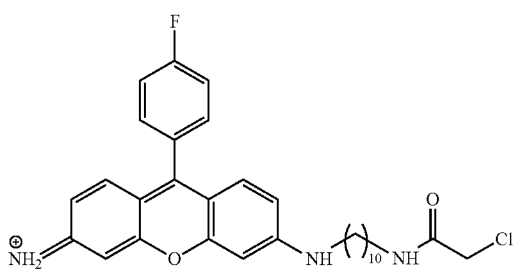 |
| 26 | 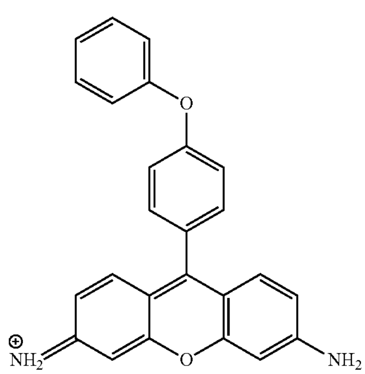 |
| 27 | 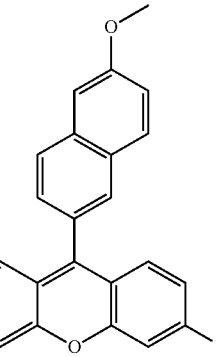 |
| 28 | 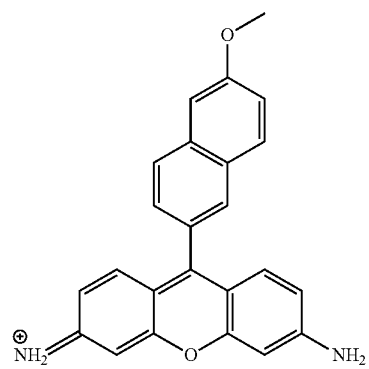 [SMILES: COc1ccc2cc(-c3c4ccc(=[NH2+])cc-4oc4cc(N)ccc34)ccc2c1] |
| 29 | 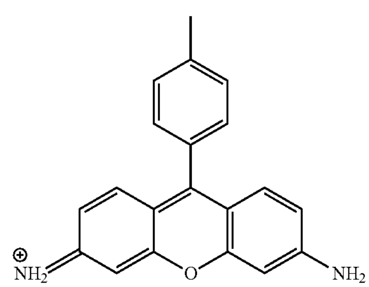 [SMILES: Cc1ccc(-c2c3ccc(=[NH2+])cc-3oc3cc(N)ccc23)cc1] |
| 30 | 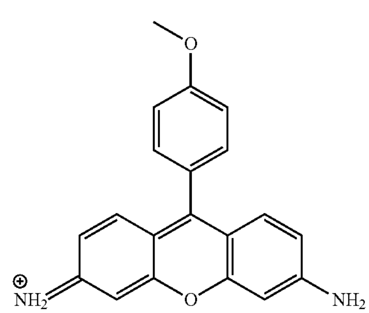 [SMILES: COc1ccc(-c2c3ccc(=[NH2+])cc-3oc3cc(N)ccc23)cc1] |

TABLE 2-continued

| No | Compound structure |
|----|---|
| 31 | (4-propylphenyl-substituted pyronin/xanthene with NH2⊕ and NH2) |
| 32 | (3-chlorophenyl-substituted xanthene with NH2⊕ and NH2) |
| 33 | (phenyl-substituted xanthene with NH2⊕ and NH2) |
| 34 | (3,4-dimethoxyphenyl-substituted xanthene with NH2⊕ and NH2) |
| 35 | (4-fluorophenyl-substituted xanthene with NH⊕ and NH, methylated) |
| 36 | (2-fluorophenyl-substituted xanthene with NH2⊕ and NH2) |

The compounds to be used in the method of the present invention may be a salt of those compounds. The salts are well known to those of ordinary skill in the art, and preferable examples thereof include salts with inorganic acids such as hydrochloric acid, hydrobromic acid, nitric acid, sulfuric acid, phosphoric acid and the like; salts with organic acids such as formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like; alkali metal salts such as sodium salt, potassium salt and the like; alkaline earth metal salts such as calcium salt, magnesium salt, barium salt and the like; aluminum salt; ammonium salt; salts with organic bases such as trimethylamine, triethylamine, pyridine, picoline, 2,6-lutidine, ethanolamine, diethanolamine, triethanolamine, N,N-diethylamine, cyclohexylamine, N,N'-dicyclohexylamine, N,N'-dibenzylethylenediamine, N,N-dimethylaminopyridine (DMAP), 1,4-diazabicyclo[2.2.2]octane (DABCO), 1,5-diazabicyclo[4.3.0]nonene-5 (DBN), 1,8-diazabicyclo[5.4.0]undec-7-ene (DBU) and the like; salts with basic amino acids such as arginine, lysine, ornithine and the like; salts with acidic amino acids such as aspartic acid, glutamic acid and the like; and the like.

In one embodiment, the compounds to be used in the method of the present invention can be prepared by the reaction described in US2008/0124751.

In the other embodiment, the following synthesis scheme can be provided.

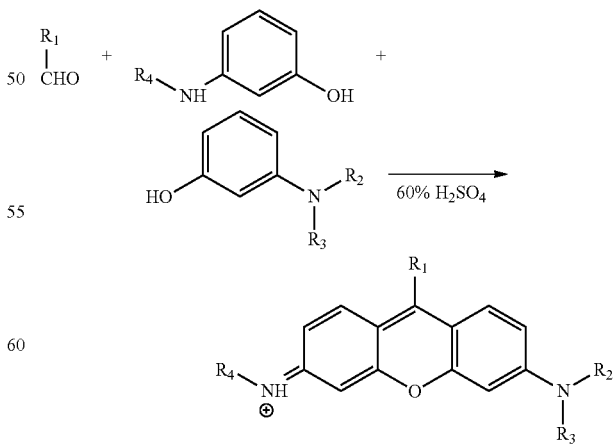

When the compounds have a functional group (hydroxyl group etc.), the functional group may be protected in advance as necessary, and subjected to deprotection by a conventional method after the above-mentioned reaction.

In the present invention, the method of sorting pluripotent cells comprise further step detecting the cells which have accumulated the compound as pluripotent cell. For example, the cells which have accumulated the compound can be detected by measuring the fluorescence of the compound or using an antibody against the compound.

The pluripotent cell has pluripotency which enables the cells to differentiate into any cells existing in the living body, and also have growth ability. Examples of the pluripotent stem cells include, but are not limited to, embryonic stem (ES) cells, embryonic stem cells derived from a cloned embryo obtained by nuclear transfer ("ntES cells"), germline stem cells ("GS cells"), embryonic germ cells ("EG cells") and induced pluripotent stem (iPS) cells. Preferred examples of the pluripotent stem cells include ES cells, ntES cells and iPS cells.

(A) Embryonic Stem Cells

ES cells are stem cells established from the inner cell mass of an early embryo (for example, blastocyst) of a mammal such as human or mouse, and have pluripotency and growth ability by self-renewal.

ES cells are embryo-derived stem cells originated from the inner cell mass of a blastocyst which is an embryo formed following the 8-cell stage and the morula stage of a fertilized egg, and have ability to differentiate into any cells constituting an adult, that is, so called pluripotency of differentiation, and growth ability by self-renewal. ES cells were discovered in mouse in 1981 (M. J. Evans and M. H. Kaufman (1981), Nature 292:154-156), and this was followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; and J. A. Thomson and V. S. Marshall (1998), Curr. Top. Dev. Biol., 38:133-165).

ES cells can be established by removing the inner cell mass from the blastocyst of a fertilized egg of a subject animal, followed by culturing the inner cell mass on fibroblasts as feeders. The cells can be maintained by subculturing using a culture medium supplemented with substances such as leukemia inhibitory factor (LIP) and basic fibroblast growth factor (bFGF). Methods of establishment and maintenance of human and monkey ES cells are described in, for example, H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; and H. Kawasaki et al. (2002), Proc. Natl. Acad. Sci. USA, 99:1580-1585.

Human ES cells can be maintained, for example, using DMEM/F-12 medium supplemented with 0.1 mM 2-mercaptoethanol, 0.1 mM non-essential amino acids, 2 mM L-glutamic acid, 20% KSR and 4 ng/ml bFGF, at 37° C. under a moist atmosphere with 5% $CO_2$. Further, it is necessary to subculture ES cells every 3 to 4 days, and the subculture can be carried out using, for example, 0.25% trypsin and 0.1 mg/ml collagenase IV in PBS supplemented with 1 mM $CaCl_2$ and 20% KSR.

Selection of ES cells can be generally carried out using expression of a gene marker(s) such as alkaline phosphatase, Oct-3/4 and/or Nanog as an index/indices. In particular, selection of human ES cells can be carried out by detecting expression of a gene marker(s) such as OCT-3/4 and/or NANOG by Real-Time PCR, or by detecting a cell surface antigen(s) SSEA-3, SSEA-4, TRA-1-60 and/or TRA-1-81 by immunostaining (Klimanskaya I, et al. (2006), Nature. 444: 481-485).

Human ES cell lines such as KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and have a property to enable preparation of a chimeric mouse by transplanting the cells to a mouse blastocyst (M. Kanatsu-Shinohara et al. (2003) Biol. Reprod., 69:612-616; K. Shinohara et al. (2004), Cell, 119: 1001-1012). Germline stem cells are capable of self-renewal in a culture medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition), 41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing certain specific nuclear reprogramming substances in the forms of DNAs or proteins to somatic cells, or by increasing expression of the endogenous mRNAs and proteins of the nuclear reprogramming substances by using an agent(s). iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007) Cell, 131:861-872; J. Yu et al. (2007) Science, 318:1917-1920; M. Nakagawa et al. (2008) Nat. Biotechnol., 26:101-106; WO 2007/069666; and WO 2010/068955). The nuclear reprogramming substances are not restricted as long as these are genes specifically expressed in ES cells, or genes playing important roles in maintenance of the undifferentiated state of ES cells, or gene products thereof, and examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb, Esrrg and Glis1. These reprogramming substances may be used in combination when iPS cells are to be established. For example, the combination may contain at least one, two or three of the above reprogramming substances, and the combination preferably contains four of the above reprogramming substances.

The information on the nucleotide sequences of mouse and human cDNAs of the above-described respective nuclear reprogramming substances, and the amino acid sequences of the proteins encoded by the cDNAs can be obtained by referring to the NCBI accession numbers described in WO 2007/ 069666. Further, the information on the mouse and human cDNA sequences and amino acid sequences of each of L-Myc, Lin28, Lin28b, Esrrb, Esrrg and Glis1 can be obtained by referring to the NCBI accession numbers described below. Those skilled in the art can prepare desired nuclear reprogramming substances by a conventional method based on the information on the cDNA sequences or amino acid sequences.

| Gene name | Mouse | Human |
|---|---|---|
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |

These nuclear reprogramming substances may be introduced into somatic cells in the form of protein by a method such as lipofection, binding to a cell membrane-permeable peptide, or microinjection, or in the form of DNA by a method such as use of a vector including a virus, plasmid and artificial chromosome; lipofection; use of liposomes; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (Proc Jpn Acad Ser B Phys Biol Sci. 85, 348-62, 2009). Examples of the artificial chromosome vector include human artificial chromosomes (HACs), yeast artificial chromosomes (YACs) and bacterial artificial chromosomes (BACs, PACs). Examples of the plasmid which may be used include plasmids for mammalian cells (Science, 322:949-953, 2008). The vectors may contain a regulatory sequence(s) such as a promoter, enhancer, ribosome binding sequence, terminator and/or polyadenylation site. Examples of the promoter to be used include the EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR and HSV-TK (herpes simplex virus thymidine kinase) promoter. Among these, the EF1α promoter, CAG promoter, MoMuLV LTR, CMV promoter, SRα promoter and the like are preferred. The vectors may further contain, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; or the like. Further, in order to remove, after introduction of the above vector into somatic cells, the genes encoding the nuclear reprogramming substances, or both the promoters and the genes encoding the reprogramming substances linked thereto, the vector may have loxP sequences in the upstream and the downstream of these sequences. In another preferred mode, a method may be employed wherein, after incorporation of the transgene(s) into a chromosome(s) using a transposon, transposase is allowed to act on the cells using a plasmid vector or an adenovirus vector, thereby completely removing the transgene(s) from the chromosome(s). Preferred examples of the transposon include piggyBac, which is a transposon derived from a lepidopteran insect (Kaji, K. et al., (2009), Nature, 458: 771-775; Woltjen et al., (2009), Nature, 458: 766-770; and WO 2010/012077). Further, the vector may contain the origin of lymphotrophic herpes virus, BK virus or Bovine papillomavirus and sequences involved in their replication, such that the vector can replicate without incorporation into the chromosome and exist episomally. Examples of such a vector include vectors containing EBNA-1 and oriP sequences and vectors containing Large T and SV40ori sequences (WO 2009/115295; WO 2009/157201; WO 2009/149233). Further, in order to introduce plural nuclear reprogramming substances at the same time, an expression vector which allows polycistronic expression may be used. In order to allow polycistronic expression, the sequences encoding the genes may be linked to each other via IRES or the foot-and-mouth disease virus (FMDV) 2A coding region (Science, 322:949-953, 2008; and WO 2009/092042 2009/152529).

For enhancing the induction efficiency of iPS cells upon the nuclear reprogramming, histone deacetylase (HDAC) inhibitors [for example, low molecular inhibitors such as valproic acid (VPA) (Nat. Biotechnol., 26(7): 795-797 (2008)), trichostatin A, sodium butyrate, MC 1293 and M344; and nucleic acid-type expression inhibitors such as siRNAs and shRNAs against HDAC (e.g., HDAC1 siRNA Smartpool (registered trademark) (Millipore) and HuSH 29mer shRNA Constructs against HDAC1 (OriGene))], DNA methyltransferase inhibitors (e.g., 5'-azacytidine) (Nat. Biotechnol., 26(7): 795-797 (2008)), G9a histone methyltransferase inhibitors [for example, low molecular inhibitors such as BIX-01294 (Cell Stem Cell, 2: 525-528 (2008)); and nucleic acid-type expression inhibitors such as siRNAs and shRNAs against G9a (e.g., G9a siRNA (human) (Santa Cruz Biotechnology))], L-channel calcium agonists (e.g., Bayk8644) (Cell Stem Cell, 3, 568-574 (2008)), p53 inhibitors [e.g., siRNAs and shRNAs against p53 (Cell Stem Cell, 3, 475-479 (2008))], Wnt Signaling activators (e.g., soluble Wnt3a) (Cell Stem Cell, 3, 132-135 (2008)), growth factors such as LIF and bFGF, ALK5 inhibitors (e.g., SB431542) (Nat. Methods, 6: 805-8 (2009)), mitogen-activated protein kinase signaling inhibitors, glycogen synthase kinase-3 inhibitors (PLoS Biology, 6(10), 2237-2247 (2008)), miRNAs such as miR-291-3p, miR-294 and miR-295 (R. L. Judson et al., Nat. Biotech., 27: 459-461 (2009)), and the like may be used in addition to the above-described factors.

Examples of the agent used for increasing expression of the endogenous proteins of nuclear reprogramming substances include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2H)-benzothiazolyl)ethanone HBr (pifithrin-alpha), prostaglandin J2 and prostaglandin E2 (WO 2010/068955).

Examples of the culture medium for induction of the iPS cells include (1) DMEM, DMEM/F12 and DME supplemented with 10 to 15% FBS (these media may further contain LIF, penicillin/streptomycin, puromycin, L-glutamine, non-essential amino acids, β-mercaptoethanol and/or the like, as appropriate); (2) culture media for ES cells containing bFGF or SCF, for example, culture media for mouse ES cells (e.g., TX-WES medium, Thromb-X) and culture media for primate ES cells (e.g., culture medium for primate (human and monkey) ES cells (ReproCELL Inc., Kyoto, Japan), mTeSR-1).

Examples of the culture method include a method wherein somatic cells and nuclear reprogramming substances (DNAs or proteins) are brought into contact with each other at 37° C. in the presence of 5% $CO_2$ in DMEM or DMEM/F12 medium supplemented with 10% FBS, and the cells are cultured for about 4 to 7 days, followed by replating the cells on feeder cells (e.g., mitomycin C-treated STO cells or SNL cells) and starting culture in a bFGF-containing culture medium for primate ES cells about 10 days after the contact between the somatic cells and the reprogramming substances, thereby allowing ES cell-like colonies to appear about 30 to about 45 days after the contact, or later. To enhance the induction efficiency of iPS cells, the culture may be carried out under a condition wherein the concentration of oxygen is as low as 5 to 10%.

As an alternative culture method, the somatic cells may be cultured on feeder cells (e.g., mitomycin C-treated STO cells or SNL cells) in DMEM medium supplemented with 10% FBS (which may further contain LIF, penicillin/streptomycin, puromycin, L-glutamine, non-essential amino acids, β-mercaptoethanol and/or the like, as appropriate), thereby allowing ES-like colonies to appear after about 25 to about 30 days of the culture, or later.

During the above culture, the culture medium is replaced with a fresh culture medium once every day from Day 2 of the culture. The number of the somatic cells used for nuclear reprogramming is not restricted, and usually within the range of about $5 \times 10^3$ to about $5 \times 10^6$ cells per 100-cm$^2$ area on the culture dish.

In cases where a gene including a drug resistance gene is used as a marker gene, cells expressing the marker gene can be selected by culturing the cells in a culture medium (selection medium) containing the corresponding drug. Cells expressing a marker gene can be detected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present specification means any cells, excluding germ cells, derived from a mammal (e.g., human, mouse, monkey, pig or rat). Examples of the somatic cells include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells) and pigment cells (e.g., retinal pigment epithelial cells), and progenitor cells (tissue progenitor cells) thereof. The level of differentiation of the cells and the age of the animal from which the cells are collected are not restricted, and either undifferentiated progenitor cells (including somatic stem cells) or terminally-differentiated mature cells may be used as the source of the somatic cells in the present invention. Here, examples of the undifferentiated progenitor cells include tissue stem cells (somatic stem cells) such as neural stem cells, hematopoietic stem cells, mesenchymal stem cells and dental pulp stem cells.

In the present invention, the mammalian individual from which somatic cells are derived is not restricted, and preferably human.

(E) ES Cells Derived from Cloned Embryo Obtained by Nuclear Transfer ntES cells are ES cells derived from a cloned embryo prepared by the nuclear transfer technique, and have almost the same properties as those in ES cells derived from fertilized eggs (T. Wakayama et al. (2001), Science, 292:740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition), 47-52). In nuclear transfer, reprogramming can be achieved by injecting the nucleus of a somatic cell into a mammalian enucleated unfertilized egg and culturing the resultant for a several hours.

(F) Fused Stem Cells

These are stem cells prepared by fusing a somatic cell with an egg or an ES cell, and have the same pluripotency as that of the ES cell used for the fusion and also have genes specific to somatic cells (Tada M et al. Curr Biol. 11:1553-8, 2001; Cowan C A et al. Science. 2005 Aug. 26; 309(5739):1369-73).

The method of the present invention can be used in the case of sorting pluripotent cells from the sample cells comprising somatic cells introduced with the reprogramming factor aforementioned.

The method of the present invention can also be used in the case of sorting pluripotent cells from the sample cells comprising pluripotent cells induced to differentiate to somatic cells.

Here, pluripotent cells may be induced not only differentiation into particular organ cells and progenitor cells thereof, but also differentiation into cell populations including a wide variety of cell types such as endodermal cells, mesodermal cells and ectodermal cells. Organs targeted in the present invention include, but are not limited to, the skin, blood vessels, cornea, kidney, heart, liver, umbilical cord, intestine, nerves, lung, placenta, pancreas, brain, limb peripheries, retina and the like. Any method of differentiation induction obvious to those skilled in the art can be used; examples include the method of induction of differentiation into nerve stem cells described in JP-A-2002-291469, the method of induction of differentiation into pancreatic stem-like cells described in JP-A-2004-121165, and the method of induction of differentiation into hematopoietic cells described in JP-T-2003-505006. In addition, methods of induction of differentiation by formation of embryoid are exemplified by the method described in JP-T-2003-523766 and the like.

In the other embodiment, the method of the present invention can be used to select pluripotent cells by selecting the cells which have accumulated the compound.

In the other embodiment, the method of the present invention can be used to select differentiated cells by excluding the cells which have accumulated to the compound.

In the other embodiment, a kit for sorting pluripotent cells is provided. The kit may comprise a compound mentioned above, a culture solution and so on. The kit may further comprise written procedures or instructions for sorting.

EXAMPLE

<Materials>

Cyclosporin A was purchased from Wako Pure Chemical Industries. Mouse monoclonal anti-MDR1 antibody (MRK16) was purchased from Kyowa Medix. Fluorescently-labeled secondary antibodies were purchased from Molecular Probes. Fetal bovine serum (FBS) from Invitrogen. Dulbecco's modified Eagle's medium (DMEM) from Nacalai Tesque.

<Characterization of Human iPS Cells Incubated with Compound 1 by Fluorescence Microscopic and FACS Analysis>

Human iPS cells (clone#201B7) cells (Takahashi, K. et al. Cell 2007, 131, 861-872) were plated at a density of 2×10$^5$ cells/well of 6-well plate on SNL feeder cells (McMahon, A. P. and Bradley, A., Cell, 62, 1073-1085, 1990). Six days after plating, the cells were incubated with 2 µM Compound 1 (Table 2) for 3 hours (fluorescence microscopic images were taken at this point). The cells were dissociated with Accutase (Invitrogen) into single cells and stained with a-SSEA-4-Alexa647 for 30 min at room temperature. After washing, FACS (FACS Aria II) analysis was performed.

<Fluorescence Microscopic Imaging of Partially Differentiated Human iPS Cells>

Human iPS cells (clone#201B7) were plated on SNL feeder cells in 96-well plate. 5 days after plating, some donut-shaped colonies of iPS cells were incidentally obtained. These cells were incubated with 4 µM Compound 1 for 4.5 hours at 37° C. Fluorescence microscopic images were taken by using Carl Zeiss Axioskop.

<Fluorescence Microscopic Imaging of Human ES Cells and Differentiated Cells>

The hES cell line KhES-1 was maintained as described previously (Suemori, H. et al. Biochem. Biophys. Res. Commun. 2006, 345, 926-932). To induce differentiation of hESCs, cells seeded onto Matrigel-coated plate were cultured for 4 days with 500 nM all-trans retinoic acid (Sigma R2625) in DMEM supplemented with 10% FBS. After staining with 1 µM Compound 1 for 2 hours, cells were rinsed with PBS and kept in fresh medium (without dye). Fluorescent microscopy was performed by using Olympus IX71 with DP72.

<Cell Culture>

KB/MDR1, stably expressing human MDR1, and KB3-1 host cells (Ueda, K et al., PNAS 84, 3004-3008, 1987) were maintained in DMEM supplemented with 10% FBS in a humidified incubator (5% $CO_2$) at 37° C.

<Accumulation of the Fluorescent Compounds>

Cells were subcultured in 35 mm/glass base dish (IWAKI) at a density of 5×10$^5$ cells per dish in DMEM containing 10% FBS for 24-48 hours. Then, cells were incubated in DMEM containing 10% FBS and the compounds for 2 hours at 37° C., washed with phosphate-buffered saline (PBS), and observed using a confocal microscope (LSM 700; Carl Zeiss).

<Immunostaining>

Cells were grown on glass coverslips and fixed with 4% paraformaldehyde in PBS+ (PBS containing 0.1 mg/ml $CaCl_2$ and $MgCl_2.6H_2O$) for 20 min at room temperature. After blocking with 10% goat serum diluted with PBS+ for 1 hour, cells were incubated with 5 µg/ml MRK16, and then with the fluorescently-labeled secondary antibody.

<PCR>

RNA was prepared from five human ES (hES) cell lines (KhES-1, KhES-2, KhES-3, KhES-4, KhES-5) and three human iPS (hiPS) cell lines (IMR90-1, IMR90-4, 201B7). First strand cDNA was synthesized with reverse transcriptase (Applied Biosystems). Gene expression profiles were analyzed by quantitative real-time PCR (RT-PCR) using TaqMan Array Gene Signature 96-Well Plate, Human ABC Transporters (Applied Biosystems), covering 44 ABC transporters and four housekeeping genes (GAPDH, 18S, HPRT1, GUSB). The expression level was normalized to GAPDH.

<Characterization of Human ES Cells and Differentiated Cells Incubated with Compound 1 by FACS Analysis>

Cells were prepared as above. After staining with 1 µM Compound 1 for 1 hour, cells were rinsed with PBS and cultured for additional 24 hours. Fluorescent microscopy was performed by using Olympus IX71 with DP72. CsA was added at the concentration of 10 µM during staining with Compound 1 and following culture until analysis. For FACS analysis, the cells were washed twice with ice-cold PBS and then dissociated with 0.25% trypsin-EDTA into a single cell suspension for direct analysis. The proportions of cells with Compound 1 were examined on a FACSCalibur flow cytometer (Becton Dickenson, Calif., USA) with reference to a baseline of untreated undifferentiated or differentiated hESCs.

<Screening for Human iPS Cells>

Fluorescent-compound libraries were provided from Young-Tae Chang's group (Ahn, Y-H., Lee, J-S. and Chang, Y-T. J. Am. Chem. Soc. 2007, 129, 4510-4511). Human iPS cells (clone#201B2) were plated on SNL feeder cells in 96-well plate. Five days after plating, fluorescent compounds were added at the final concentration of 4 µM. After incubation overnight, fluorescence microscopic images were taken by using Carl Zeiss Axioskop.

<Two Dimensional Gel Electrophoresis (2-DE)>

Human iPS cells were treated with the chloroacetyl derivative of Compound 1 (Compound 22) (1 µM) for 4 hours, and then washed twice with PBS. After treatment with CTK solution (Reprocell) to remove SNL feeder cells, human iPS cells were harvested with treatment of accutase. Mitochondria fraction was obtained from the cell pellet by using ProteoExtract® Cytosol/Mitochondria Fractionation kit according to the manufacturer's instruction. Isoelectric focusing (IEF) was performed by using ampholine (pH 3.5-10, Phamalyte 3-10 for IEF, GE Healthcare). Then, the IEF strips were separated on 10% SDS-PAGE gel for 2D analysis. 2D fluorescence image was acquired using the Typhoon 9400 scanner (GE healthcares) at excitation/emission wavelengths of 532 nm/580 nm. The fluorescence-labeled spots were excised from the gel for mass analysis.

<Fluorescence Microscopic Imaging of Partially Differentiated Human iPS Cells>

Human iPS cells (clone#201B7) were plated on SNL feeder cells in 24-well plate. One day after plating, the cells were incubated with 1 µM Compound 1 for 4 hours at 37° C. After removing Compound 1 by washing with PBS, the cells were incubated with 9.6 nM MitoRed for 30 min at 37° C. The cells were rinsed with PBS and kept in fresh medium (without dye). Fluorescence microscopic images were taken by using Carl Zeiss Axioinvert 100M Synthesis of Compound 23, 24, 25, and 22

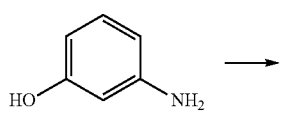

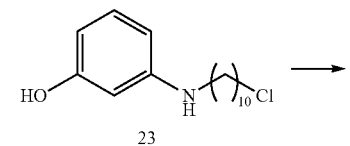

23

-continued

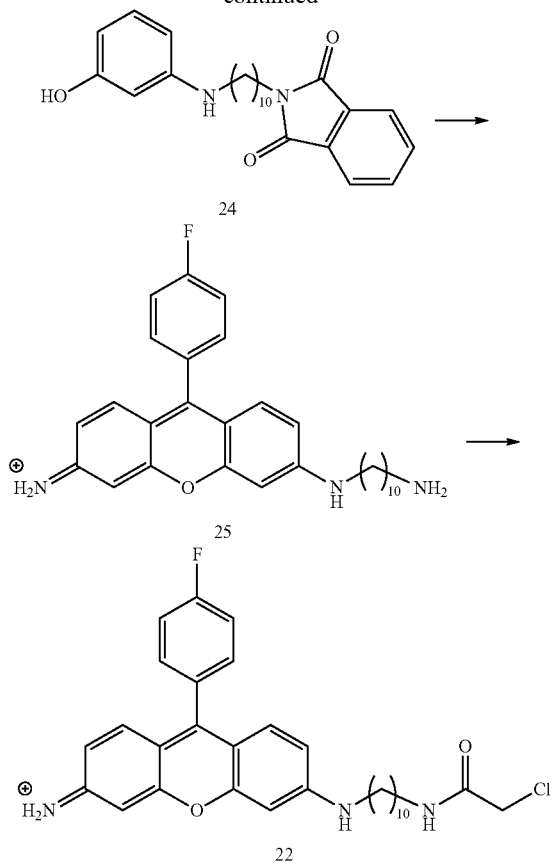

Compound 23

1,10-Dichlorodecane (8.73 g, 41.3 mmol) and triethylamine (6 mL) were added to a solution of m-aminophenol (3.85 g, 35.3 mmol) in DMF (40 mL). The mixture was stirred at 100° C. for 3 days. The reaction was quenched with saturated aqueous $NaHCO_3$ and extracted with EtOAc. The combined organic layer was washed with brine, dried over anhydrous $MgSO_4$, filtered, and concentrated under reduced pressure. The residue was purified by flash column chromatography (silica gel, hexane:EtOAc=9:1 to 1:1) to give the title compound (1.92 g, 6.76 mmol, 19% yield). Brown oil; $R_f$=0.57 (33% EtOAc-hexane); $^1H$ NMR (600 MHz, DMSO-$d_6$) δ 8.84 (s, 1H), 6.80 (dd, J=7.6, 8.3 Hz, 1H), 5.97 (d, J=7.6 Hz, 1H), 5.94 (s, 1H), 5.92 (d, J=8.2 Hz, 1H), 5.36 (s, 1H), 3.61 (m, 2H), 2.89 (m, 2H), 1.69 (m, 2H), 1.49 (m, 2H), 1.35-1.25 (m, 12H); $^{13}C$ NMR (150 MHz, DMSO-$d_6$) δ 158.3, 150.6, 129.5, 103.7, 103.0, 98.9, 45.6, 43.1, 32.2, 29.2, 29.1×2, 28.9, 28.4, 26.9, 26.4; FABMS m/z 283 [$M^+$]; HRMS calcd. for $C_{16}H_{26}NOCl$ [$M^+$] 283.1703. found 283.1708.

Compound 24

Potassium phthalimide (1.88 g, 10.1 mmol) was added to a solution of Compound 23 (1.92 g, 6.76 mmol) in DMF (20 mL). The mixture was stirred at 100° C. overnight. The reaction was quenched with saturated aqueous $NaHCO_3$ and extracted with EtOAc. The combined organic layer was washed with brine, dried over anhydrous $MgSO_4$, filtered, and concentrated under reduced pressure. The residue was purified by flash column chromatography (silica gel, hexane:EtOAc=5:1 to 1:1) to give the title compound (1.83 g, 4.64 mmol, 69% yield). Brown oil; $R_f$=0.51 (33% EtOAc-hexane); $^1H$ NMR (600 MHz, DMSO-$d_6$) δ 8.83 (s, 1H), 7.83 (m, 2H), 7.81 (m, 2H), 6.79 (dd, J=8.3, 7.6 Hz, 1H), 5.97 (d, J=8.2 Hz, 1H), 5.94 (s, 1H), 5.91 (d, J=7.5 Hz, 1H), 5.34 (brs, 1H), 3.54 (m, 2H), 2.88 (m, 2H), 1.56 (m, 2H), 1.47 (m, 2H), 1.29-1.22 (m, 12H); $^{13}C$ NMR (150 MHz, DMSO-$d_6$) δ 168.1, 168.3, 150.6, 134.5, 131.8, 129.5, 123.1, 103.7, 103.1, 98.9, 60.9, 43.1, 37.5, 32.7, 29.2, 29.1, 29.0×2, 28.9, 28.7, 28.0, 26.9, 26.4, 25.7; FABMS m/z 394 [$M^+$]; HRMS calcd. for $C_{24}H_{30}N_2O_3$ [$M^+$] 394.2256. found 394.2250.

Compound 25

4-Fluorobenzaldehyde (242 g, 1.95 mmol) and m-aminophenol (213 g, 1.95 mmol) were added to a solution of Compound 24 (770 g, 1.95 mmol) in 60% $H_2SO_4$ (10 mL). The mixture was stirred at 130° C. overnight. The reaction was diluted with ice-water and filtered. The precipitate was washed with distilled water (DW), dissolved in methanol, and concentrated under reduced pressure. The residue was purified by HPLC (Inertsil ODS-3, methanol: 0.1% TFA-DW=0:1 to 1:0) to give the title compound (34 g, 0.059 mmol, 3% yield). Purple oil. $^1H$ NMR (600 MHz, acetic acid-$d_4$) δ □ 7.51 (dd, J=8.9, 5.5 Hz, 2H), 7.40 (dd, J=8.9, 8.9 Hz, 2H), 7.31 (d, J=8.9 Hz, 2H), 6.98□6.93 (m, 2H), 3.40 (m, 2H), 3.04 (m, 2H), 1.74-1.67 (m, 4H), 1.44-1.32 (m, 12H); $^{13}C$ NMR (150 MHz, DMSO-$d_6$) δ 164.0, 162.4, 158.6, 158.3, 158.1, 157.9, 132.2, 132.08, 132.02, 128.4, 118.2, 117.0, 116.2, 116.1, 113.2, 113.0, 97.3, 94.1, 43.0, 39.0, 29.1, 29.0× 2, 28.9, 28.7, 28.2, 27.2, 26.6, 26.0; FABMS m/z 460 [$M^+$]; HRMS calcd. for $C_{29}H_{35}FN_3O$ [$M^+$] 460.2764. found 460.2765.

Compound 22

Chloroacetyl chloride (30 μL, 0.39 mmol) and triethylamine (100 μL) were added to a solution of Compound 25 (82.5 mg, 0.12 mmol) in DMF (1.5 mL). The mixture was stirred at 37° C. for 3 days. The reaction was diluted with methanol and filtered. The filtrate was purified by HPLC (Inertsil ODS-3, methanol:0.1% TFA-DW=0:1 to 1:0) to give the title compound (21 mg, 0.032 mmol, 27% yield). Purple oil. FABMS m/z 536 [$M^+$]; HRMS calcd. for $C_{31}H_{36}ClFN_3O_2$ [$M^+$] 536.2480. found 536.2488.

Synthesis of Compound 35

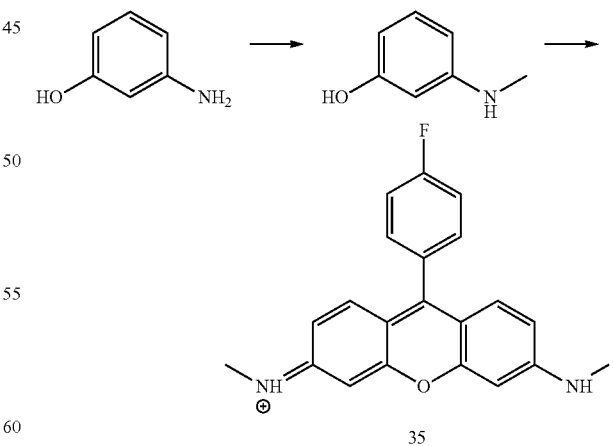

Compound 35

N-methyl aminophenol was synthesized as a previous paper (Charng-Sheng Tsai, et al., Chem. Comm., 46, 5575-5577, 2010). Briefly, A mixture of m-aminophenol (1.51 g, 13.84 mmol), $CH_3I$ (2.16 g, 15.22 mmol), and $K_2CO_3$ (2.10 g, 15.19 mmol) in DMF was stirred at room temperature for 19 hours. The mixture was diluted with distilled water and extracted with EtOAc. The combined organic layer was washed with brine, dried over anhydrous $Na_2SO_4$, and concentrated under reduced pressure. The residue was purified by flash column chromatography (silica gel, hexane:EtOAc=1:0 to 3:7) to give the title compound (brown oil, 658 mg, 5.34 mmol, 39% yield).

Above N-methyl aminophenol (411 mg, 3.34 mmol) was added to a solution of 4-fluorobenzaldehyde (150 mg, 1.21 mmol) in methanesulfonic acid (11 mL). The mixture was stirred at 120° C. for 22 hours. The reaction was diluted with distilled water and neutralized with $K_2CO_3$. The resulting mixture was extracted with EtOAc. The combined organic layer was washed with brine, dried over anhydrous $MgSO_4$, filtered, and concentrated under reduced pressure. The residue was purified by HPLC (Inertsil ODS-3, methanol: 0.1% TFA-DW=0:1 to 1:0) to give the title compound (23 mg, 0.052 mmol, 4% yield). Purple oil; $^1H$ NMR (300 MHz, $CD_3OD$) δ 7.45-7.36 (m, 4H), 7.21 (d, J=9.1 Hz, 2H), 6.81 (d, J=9.3 Hz, 2H), 6.69 (s, 2H), 2.99 (s, 6H).

Synthesis of Compound 36

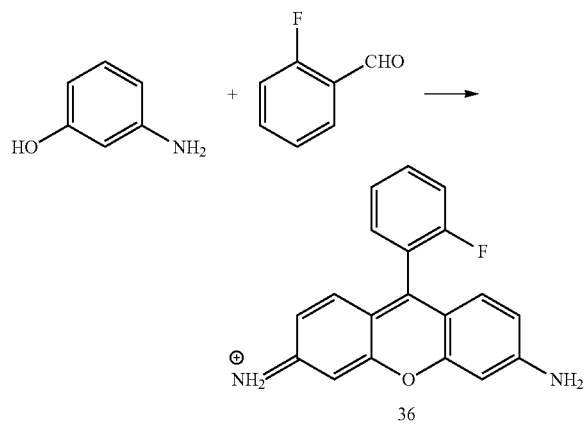

Compound 36 m-Aminophenol (1.31 g, 12 mmol) was added to a solution of 2-fluorobenzaldehyde (502 mg, 4.04 mmol) in methanesulfonic acid (12 mL). The mixture was stirred at 120° C. for 24 hours. The reaction was diluted with distilled water and neutralized with $K_2CO_3$. The precipitate was filtered and dissolved in methanol. The solution was filtered through celite, and the filtrate was purified by HPLC (Inertsil ODS-3, methanol: 0.1% TFA-DW=0:1 to 1:0) to give the title compound (10 mg, 0.025 mmol, 0.6% yield). Purple oil; 1H NMR (300 MHz, $CD_3OD$) δ 7.76-7.69 (m, $^1H$), 7.51-7.40 (m, 3H), 7.24 (d, J=9.0 Hz, 2H), 6.86 (d, J=9.0 Hz, 2H), 6.82 (s, 2H).
<Result>

To discover a fluorescent probe selective for human pluripotent stem cells, a chemical library of 326 fluorescent compounds were screened. The image-based screening isolated 31 rhodamine-based molecules (Compounds 1-21 and 26-34 shown in Table 2) that stained human iPS cells stronger than feeder cells (FIG. 1A). Furthermore, synthesized compounds 35 and 36 shown in Table 2 could be stained human iPS cells stronger than feeder cells (FIG. 1A).

The selectivity of Compound 1 for human iPS cells was quantitatively analyzed by flow cytometry (FIG. 1B-D). Mixtures of human iPS cells and feeder cells were treated either by Compound 1 (FIG. 1B), an AlexaFluor647-labelled anti-SSEA-4 antibody (FIG. 1C), or both (FIG. 1D). Compound 1-positive population (43.4%) was clearly separated from Compound 1-negative population (56.6%) by flow cytometry. SSEA-4-positive (37.6%) and negative (62.4%) populations displayed a similar distribution pattern, and when the cells were doubly stained, essentially all the SSEA-4-positive cells were stained by Compound 1 as well (42.4%), but SSEA-4-negative cells were not (55.2%). These results demonstrate that Compound 1 is capable of staining iPS cells specifically and can be suitably used to separate human iPS cells from feeder cells.

Figure 2:
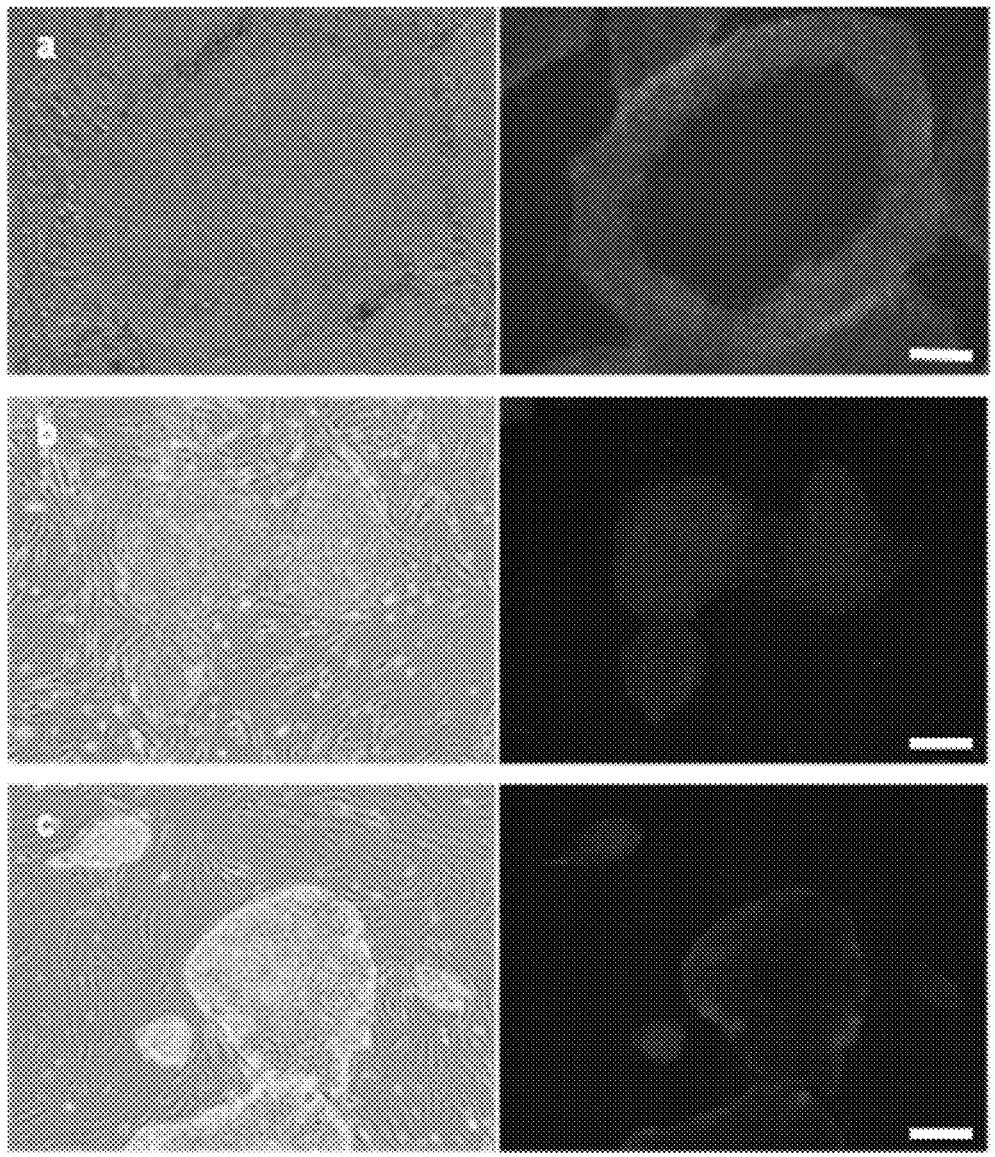
FIG. 2 shows bright-field images (left) (photographs) and fluorescence microscopic images (right) (photographs) of partially differentiated human iPS cells incubated with Compound 1 (4 μM) for 4.5 hours (a), human ES cells incubated with Compound 1 (1 μM) for 2 hours (b), and differentiated cells (derived from human ES cells by treatment with 500 nM retinoic acid for 4 days) incubated with Compound 1 (1 μM) for 2 hours (c). Scale bar: 300 μm.

When iPS cells are over-grown, central parts of iPS cell colonies tend to initiate differentiation to form donut-shaped colonies of iPS cells. Compound 1 selectively stained undifferentiated parts of those colonies but not the central parts (FIG. 2a). To confirm the observation, similar experiments with human ES cells were performed. When human ES cells were treated with Compound 1, ES cell colonies were stained more strongly than feeder cells were (FIG. 2b). Partial differentiation by retinoic acid generated less densely stained parts of colonies (FIG. 2c). These observations suggested the possibility that Compound 1 is capable of distinguishing pluripotent stem cells from differentiated cells.

Figure 3:
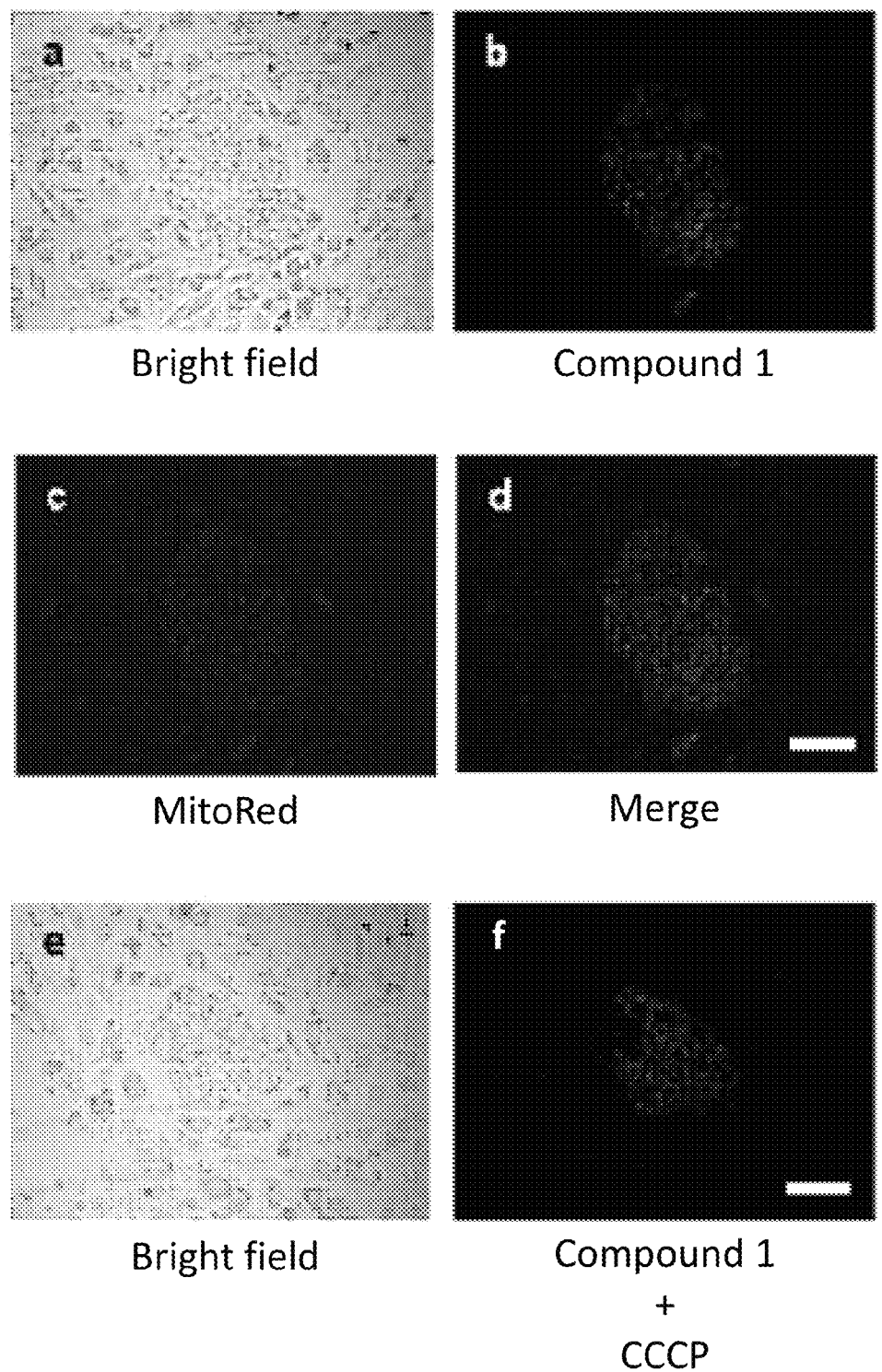
FIG. 3, panels a-d (photographs) show bright-field image (a), fluorescence microscopic image of human iPS cells stained with Compound 1 (b), 9.6 nM Mitotracker Red (c), and merged image thereof (d).

Compound 1 appears to be cell-permeable and its subcellular localization overlaps with that of MitoTracker Red (MitoRed) (Minamikawa, T. et al. *J. Cell Sci.* 1999, 112, 2419-2430), a mitochondria marker (FIG. 3a-d). While MitoRed labeled mitochondria both in human iPS cells and feeder cells, Compound 1 stained those only in iPS cells. These results suggest that Compound 1 localizes in mitochondria in human pluripotent cells. The staining of Compound 1 was examined in the presence of CCCP (Carbonyl cyanide m-chlorophenyl hydrazone), an uncoupling reagent that disrupts the mitochondrial membrane potential. The staining pattern of Compound 1 remained the same in the presence of CCCP. This result indicates that the staining properties of Compound 1 are independent of the membrane potential (FIG. 3e). To isolate mitochondrial proteins that interact with Compound 1, a chloroacetyl derivative of Compound 1 (Compound 22) were synthesized. Although the selectivity of Compound 22 is slightly less than that of Compound 1, it is still localized in mitochondria of human iPS cells. Stained mitochondoria were isolated from human iPS cells by treating with Compound 22, and fluorescently labeled mitochondrial proteins were separated by 2-dimensional SDS polyacrylamide gel electrophoresis. Using mass-sequencing analysis, the fluorescently labeled protein revealed previously reported peptide sequences of ADH1 protein (Kim, Y. K. et al. *Angew. Chem. Int. Ed.* 2011, 50, 2761-2763). However, the mechanism for the selectivity of Compound 1 is still unclear, because ADH1 is an abundant enzyme expressed in numerous cell types.

Figure 4:
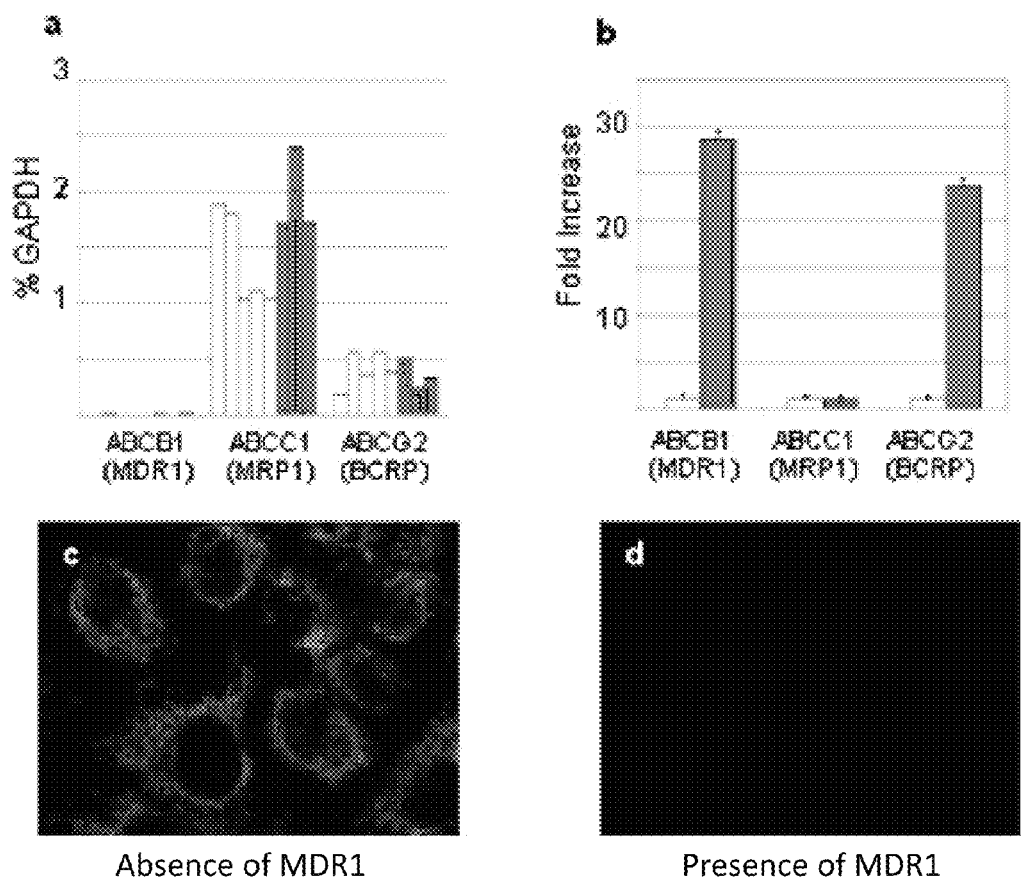
FIG. 4, panel a shows graph of expression levels of ABCB1 (MDR1), ABCC1 (MRP1), and ABCG2 (BCRP) transporter in ES cells (open bar) and hiPS cells (shaded bar).

The expression patterns of four ABC proteins involved in xenobiotic efflux in human iPS cells and human ES cells were examined by quantitative RT-PCR (FIG. 4a). Both of these human pluripotent cells express ABCC1 (MRP1) and ABCG2 at high levels but had little, if any, expression of ABCB1 (MDR1) and ABCC2 (MRP2) transporters. The expression patterns between human ES cells and differentiated cells prepared from human ES cells with retinoic acid (trophectoderm-like cells with high expression levels of CDX2) were compared (FIG. 4b). ABCG2 and ABCB1 (MDR1) are highly expressed in differentiated cells (29 and 24 folds, respectively). These results indicate that ABCB1 (MDR1) may play important role in the elimination of Compound 1.

MDR1-expressing model cell lines (KB/MDR1) were established from KB3-1, a cell line with no MDR1 expression. KB/MDR1 and KB3-1 were treated with Compound 1 for 2 hrs. Then, their images were observed under a fluorescent microscope (FIG. 4c, 4d). KB3-1 cells with no MDR1 expression were strongly stained by Compound 1 whereas fluorescent signals were undetectable in MB/MDR1 cells, demonstrating that Compound 1 is a good substrate for ABCB1 (MDR1). Similar experiments were conducted with ABCG2 and ABCC1 (MRP1). Regardless of the expression levels of ABCG2 and ABCC1 (MRP1), Compound 1 stained cells, indicating that Compound 1 is not a substrate for these two transporters. These results collectively suggest that Compound 1 is a selective substrate for ABCB1 (MDR1) and that expression levels of ABCB1 (MDR1) modulate the staining intensity of Compound 1.

Figure 5:
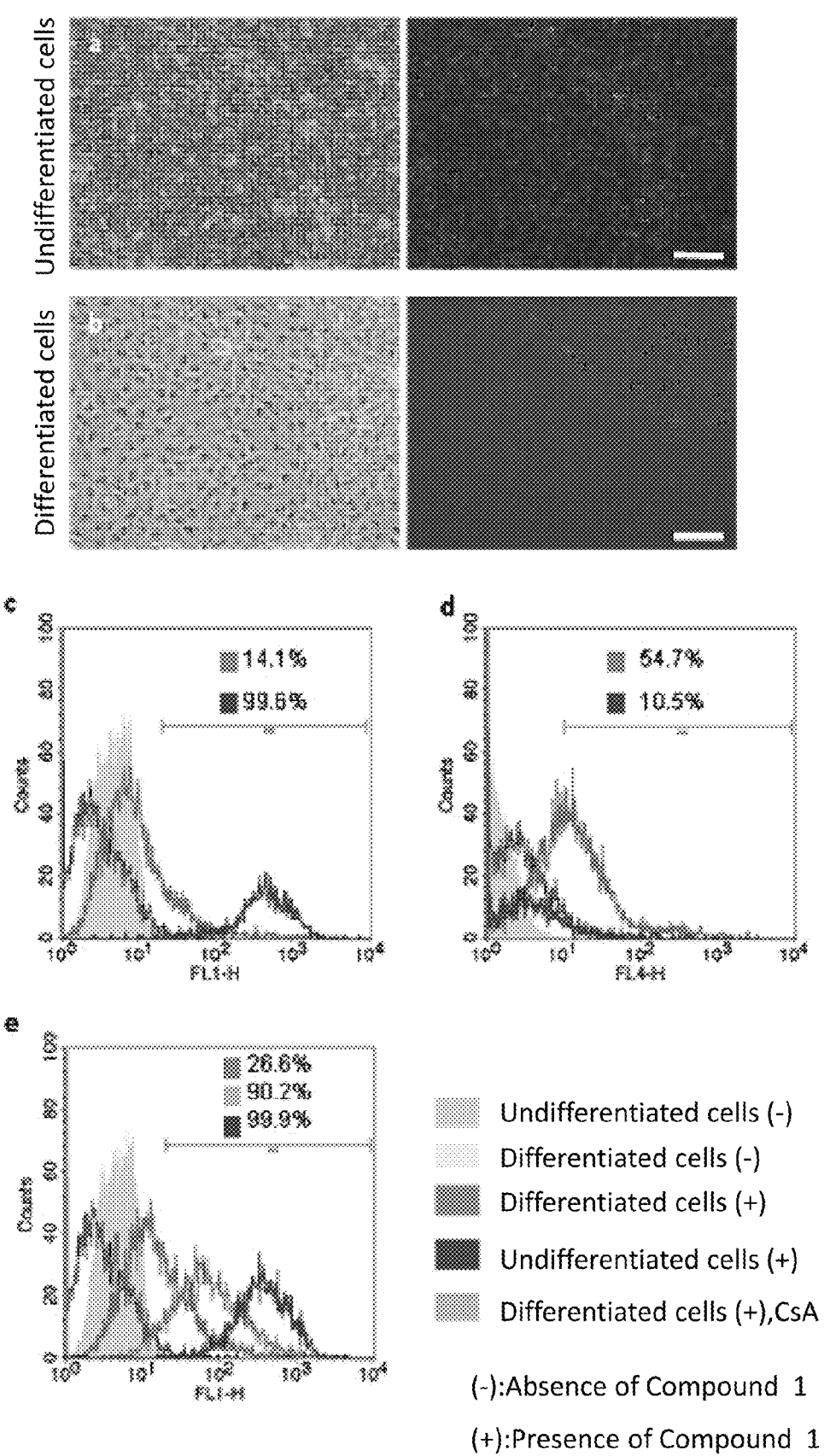
FIG. 5, panels a and b (photographs) shows Bright-field images (left) and fluorescence microscopic images (right) of undifferentiated ES cells (a) and differentiated cells derived from human ES cells (b) stained with Compound 1 (1 μM) for 1 hour. Scale bar: 100 μm.

To examine the relationship between Compound 1 selectivity and MDR1 induction upon differentiation, human ES cells and differentiated cells derived from human ES cells by retinoic acid were treated with Compound 1 (FIG. 5a, b). Human ES cells exhibited strong fluorescence, whereas the differentiated cells displayed little. Flow cytometric analysis of the cells revealed that human ES cells were stained ~100 times stronger than the differentiated cells (FIG. 5c). Similar flow cytometric analysis with a fluorescently labeled MDR1 antibody confirmed selective expression of MDR1 in the differentiated cells (FIG. 5d). When the differentiated cells were treated with Compound 1 and cyclosporine A, a known inhibitor of MDR1, even the differentiated cells were labeled by Compound 1 (FIG. 5e). These results collectively demonstrate that the selectivity of Compound 1 is governed by its selective transport by ABCB1 (MDR1) whose expression is repressed in human pluripotent cells and induced upon differentiation.

Figure 6:
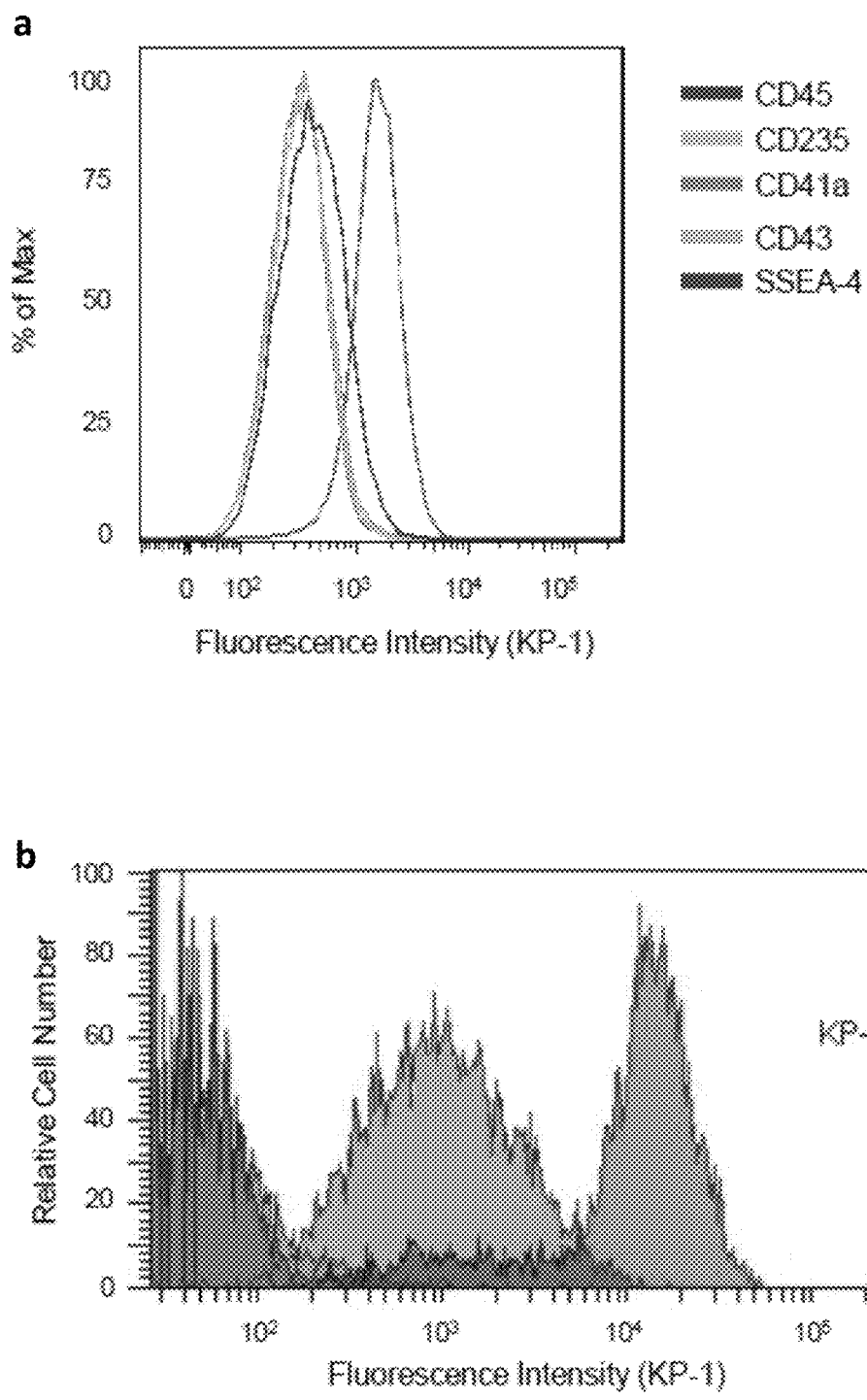
FIG. 6, panel a shows fluorescence histograms from flow cytometric analysis on human ES cells and hematopoietic cells derived from the ES cells, which stained with KP-1, anti-CD45 antibody, anti-CD235 antibody, anti-CD41a antibody, anti-CD43 antibody and anti-SSEA-4 antibody.

KP-1 was examined to stain of hematopoietic cells derived from human ES cells (Takayama et al., Blood 111, 5298-5306, 2008 or Takayama et al., J Exp Med 207, 2817-2830, 2010) (FIG. 6A). FACS analysis showed that KP-1 distinguishes between SSEA-4-positive human ES cells and human early hematopoietic cells expressing CD45, CD235, CD41a, or CD43, suggesting that KP-1 is useful for monitoring early hematopoiesis.

Figure 7:
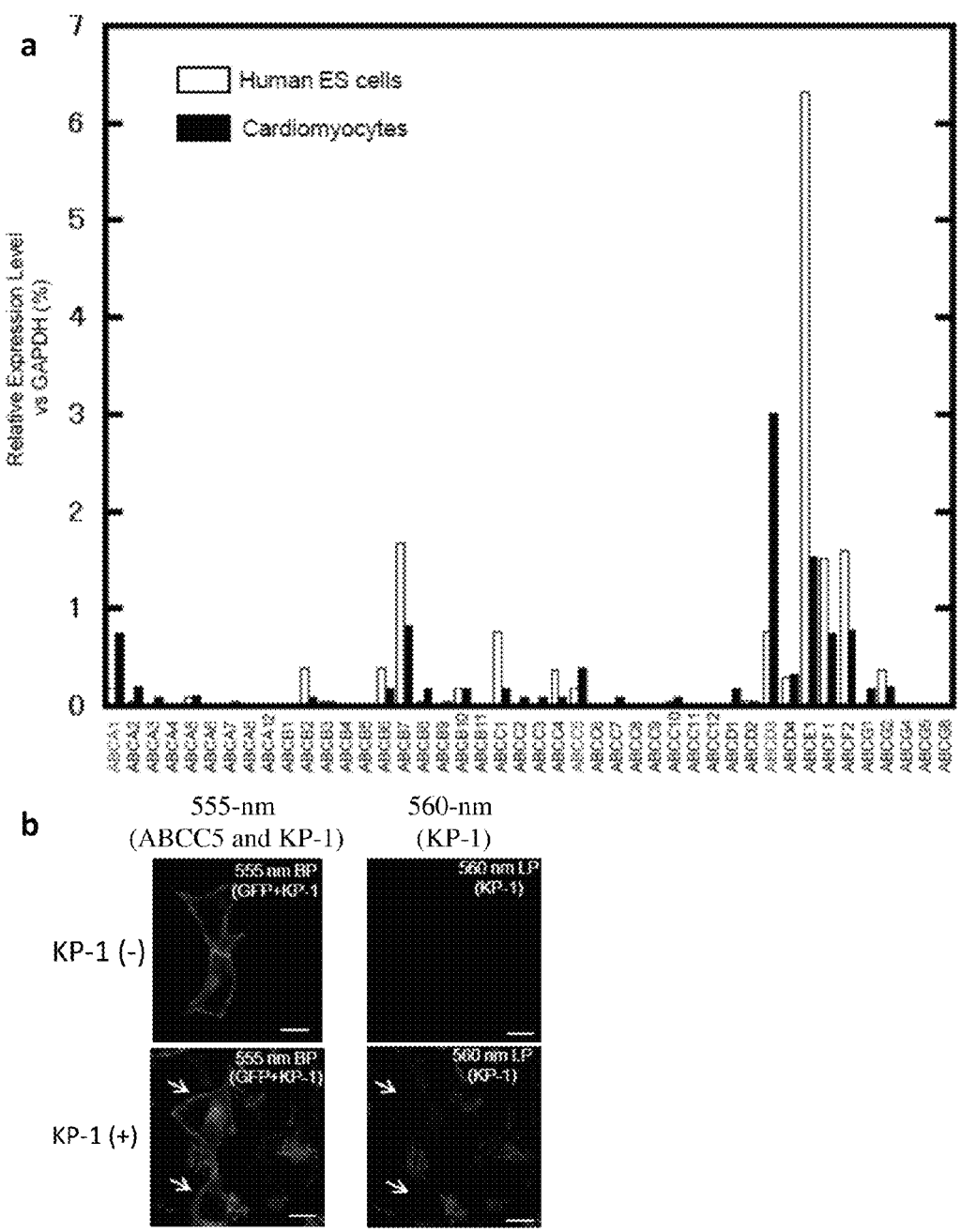
FIG. 7, panel a shows expression profile od ABC transporters in cardiomyocytes. Comparison of mRNA expression levels of ABC transporters between human ES cells (Kh-ES-3 cell line, open bar) and cardiomyocytes (solid bar).

Next the ability of KP-1 was examined to monitor other clinically important differentiation processes: cardiomyogenesis. Cardiac differentiation was carried out as described in the previous study with modifications (Wang et al., Bba-Biomembranes 1461, 177-200, 2011). Briefly, human iPS cells were cultured on 3.5 cm culture dishes coated with human laminin 211 (BioLamina, Sweden). To enhance generation of cardiac colonies, WNT signaling inhibitors were added for days 3-9 of cardiac differentiation. Cardiac colonies were harvested on day 15 and cultured for 7-10 days in floating culture. KP-1 was capable of distinguishing between human iPS cells and human iPS cell-derived cardiomyocytes, as confirmed by flow cytometric analysis (FIG. 6B). The expression patterns of forty-four human ABC transporters in cardiomyocytes derived from human iPS cells was examined by RT-PCR (FIG. 7A). Surprisingly, neither ABCG2 nor ABCB1 was induced during cardiomyogenesis. Instead, two cell-surface membrane ABC transporters, ABCA1 and ABCC5, were induced during differentiation. Although ABCD3 was also induced, this peroxisomal ABC protein was unlikely to be involved in the selectivity of KP-1. The ability of ABCA1 and ABCC5 to cause efflux of KP-1 was examined by overexpressing each transporter in HEK293 cells. The results indicated that KP-1 is a good substrate for ABCC5 (FIG. 7B), but not for ABCA1 (data not shown). KP-1 might act as a substrate for a broad range of ABC transporters that are induced by differentiation.

What is claimed is:

1. A method of sorting non-differentiated pluripotent cells from differentiated somatic cells the method comprising: (i) contacting sample cells with a compound which is eliminated from the pluripotent cells through the cellular MDR1 transporter, wherein the sample cells are pluripotent cells induced to differentiate to somatic cells and, wherein the compound has a structure of the formula (I):

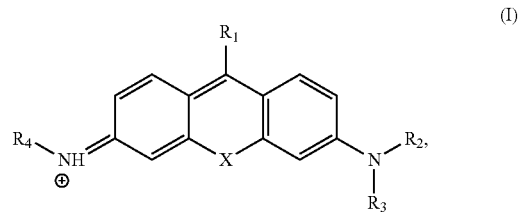

wherein $R_1$ is selected from the group consisting of the formula (II), (III) and (IV):

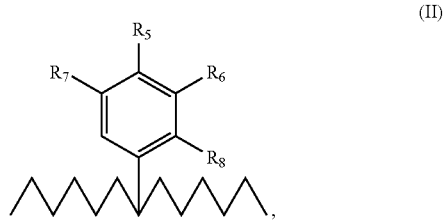

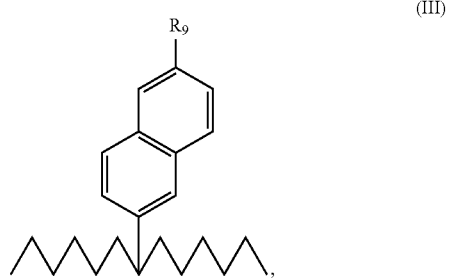

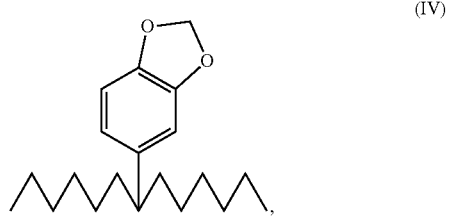

wherein $R_5$, $R_6$, $R_7$, $R_8$ and $R_9$ are respectively selected from the group consisting of hydrogen, halogen, C1 to C6 alkyl, phenyl, $-OR_{10}$ and $-SR_{10}$, wherein $R_{10}$ is C1 to C6 alkyl or aryl, wherein $R_2$, $R_3$ and $R_4$ are respectively selected from the group consisting of hydrogen, C1 to C6 alkyl and $-(CH2)_{bill}NR_{11}R_{12}$, and m is an integer of 1 to 12; and $R_{11}$ and $R_{12}$ are respectively selected from the group consisting of hydrogen, C1 to C6 alkyl and chloroacetyl, or $R_2$, and $R_3$ form the cyclic conformation of the formula (V) together with the nitrogen atom to which R, and R3 are bound:

(V)

wherein l is an integer of 1 to 6, and X is selected from the group consisting of O, S, NH and $NR_{13}$, wherein $R_{13}$ is C1 to C6 alky; and wherein the sample cells which have accumulated the compound are the non-differentiated pluripotent cells (ii) detecting and sorting the cells the non-differentiated pluripotent cells.

2. The method of claim 1, wherein:

$R_2$ and $R_3$ are respectively selected from the group consisting of hydrogen, methyl, ethyl, dimethylaminoethyl and 10-chloroacethylaminodecyl or $R_2$ and $R_3$ form the cyclic conformation of 1-piperidinyl;

$R_4$ is methyl;

$R_5$ is selected from the group consisting of hydrogen, fluorine, methoxy, phenoxy, methylthio, methyl, propyl and phenyl;

$R_6$ and $R_7$ are respectively selected from the group consisting of hydrogen, fluorine, chlorine, methoxy and methyl;

$R_8$ is fluorine;

$R_9$ is methoxy; and

X is selected from the group consisting of O, S and methylamino.

3. The method of claim 2, wherein the compound is selected from the group consisting of the compounds shown in Table 1 below:

TABLE 1

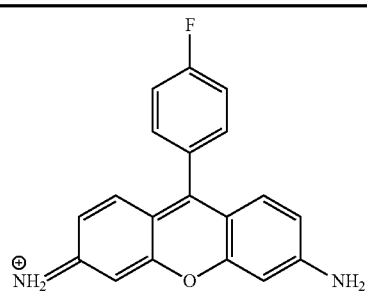

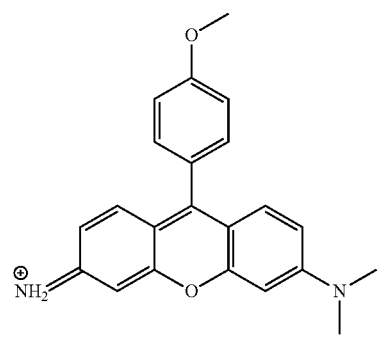 [SMILES: COc1ccc(-c2c3ccc(=[NH2+])cc-3oc3cc(N(C)C)ccc23)cc1]

TABLE 1-continued

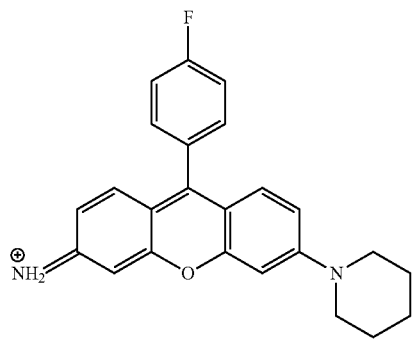 [SMILES: [NH2+]=c1ccc2c(-c3ccc(F)cc3)c3ccc(N4CCCCC4)cc3oc-2c1]

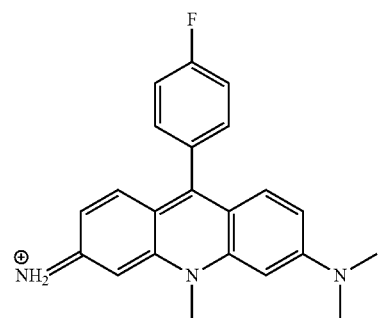 [SMILES: CN(C)c1ccc2c(-c3ccc(F)cc3)c3ccc(=[NH2+])cc-3n(C)c2c1]

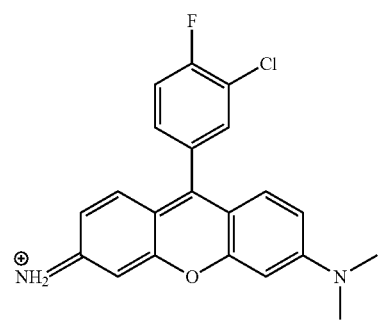 [SMILES: CN(C)c1ccc2c(-c3ccc(F)c(Cl)c3)c3ccc(=[NH2+])cc-3oc2c1]

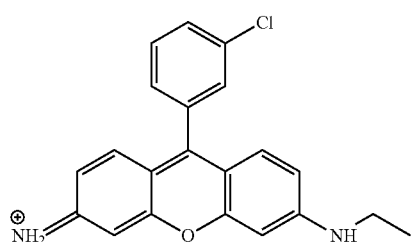

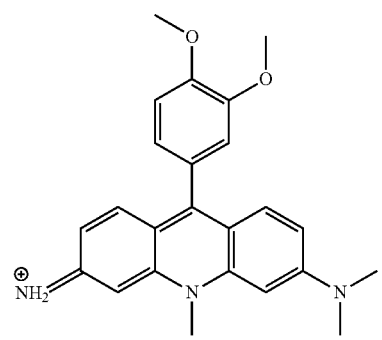 [SMILES: COc1ccc(-c2c3ccc(=[NH2+])cc-3n(C)c3cc(N(C)C)ccc23)cc1OC]

TABLE 1-continued
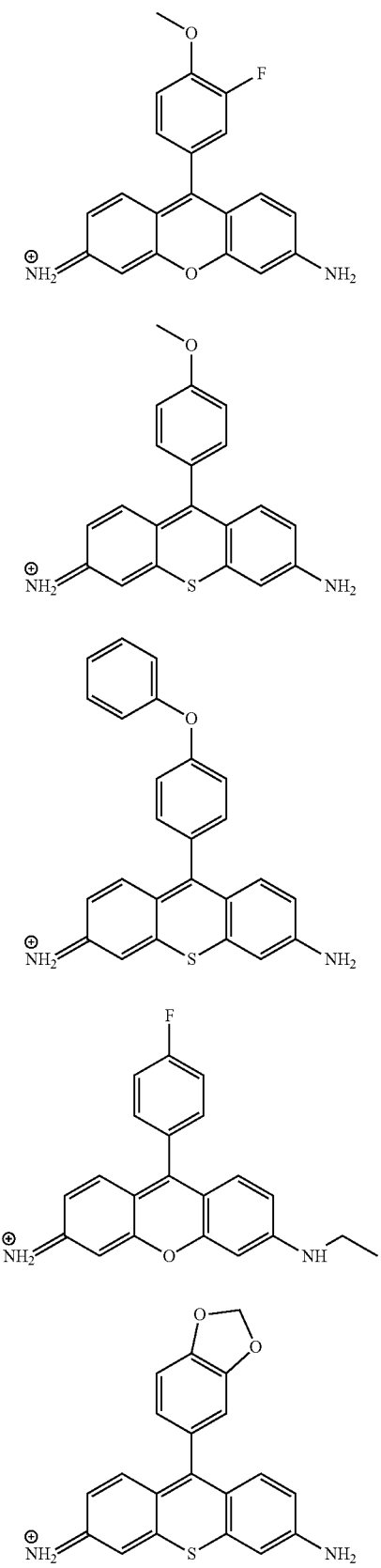
TABLE 1-continued
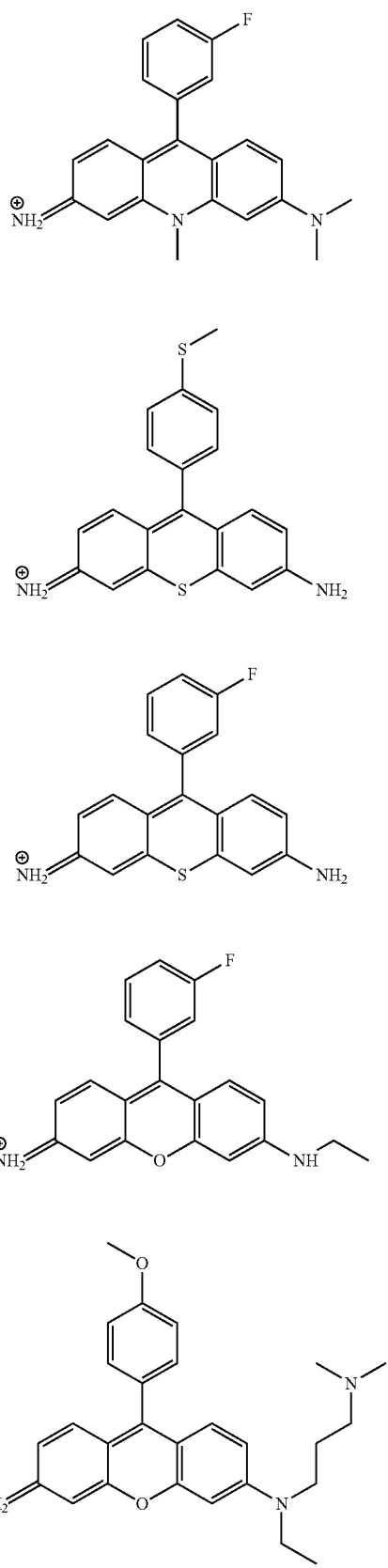

TABLE 1-continued
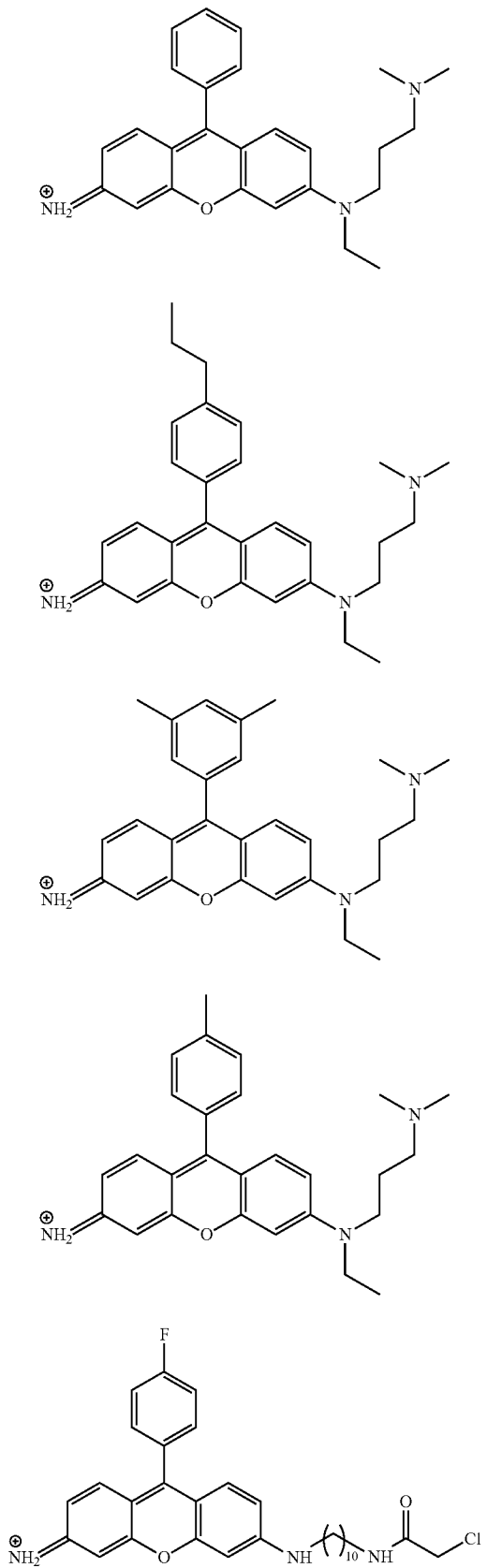
TABLE 1-continued
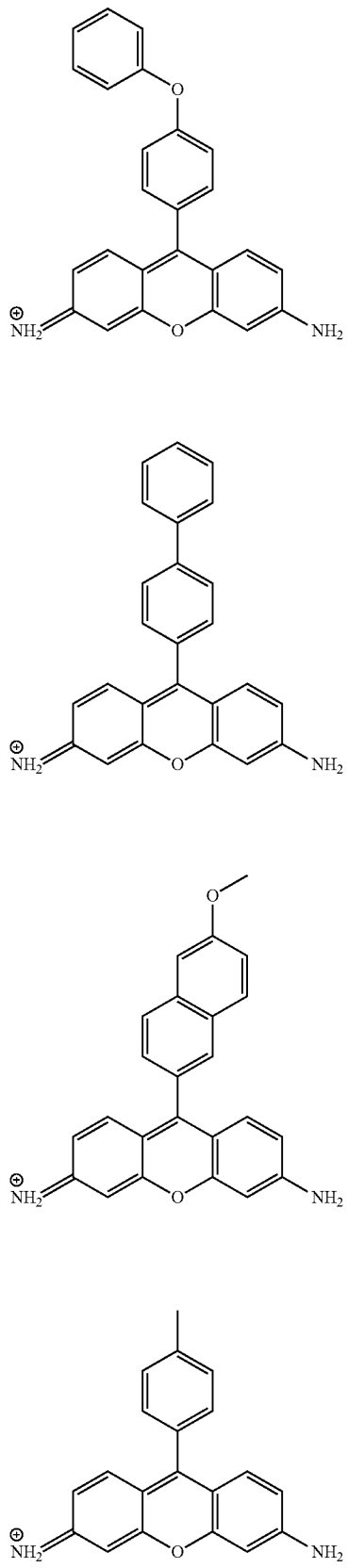

TABLE 1-continued

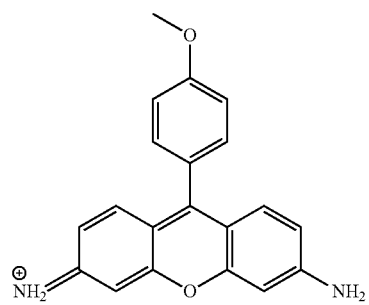

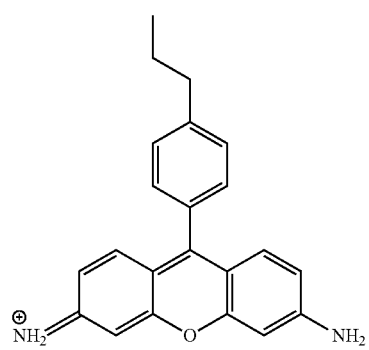 [SMILES: CCCc1ccc(-c2c3ccc(=[NH2+])cc-3oc3cc(N)ccc23)cc1]

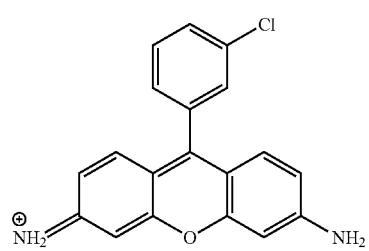

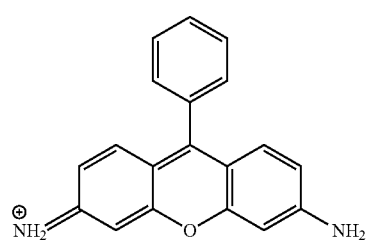

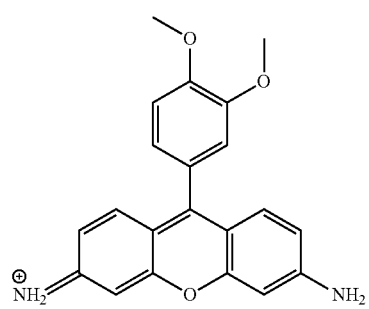

TABLE 1-continued

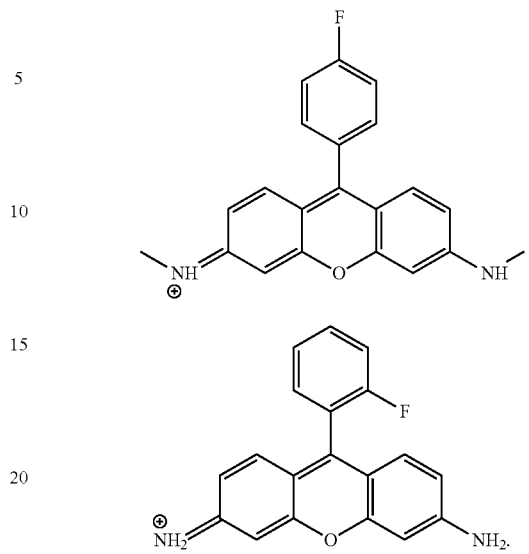

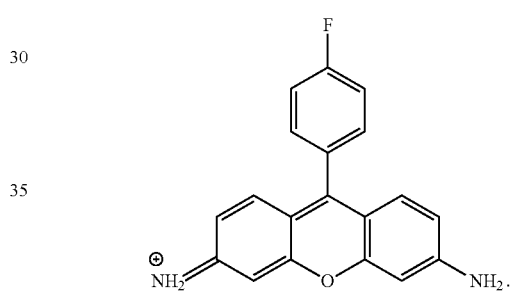

4. The method of claim 3, wherein the compound has the following formula

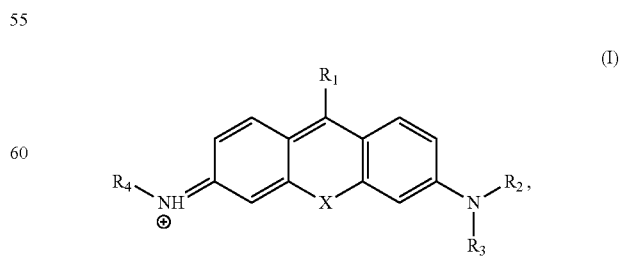

5. A method of selecting pluripotent cells comprising sorting pluripotent cells by the method of claim 1 and selecting the sorted cells.

6. A method of selecting differentiated cells, comprising sorting pluripotent cells by the method of claim 1 and excluding the sorted cells from the sample cells.

7. A method of detecting non-differentiated pluripotent cells the method comprising: (i) contacting sample cells with a compound which is eliminated from the pluripotent cells through the cellular MDR1 transporter, wherein the sample cells are pluripotent cells induced to differentiate to somatic cells and, wherein the compound has a structure of the formula (I):

(I)

$$\text{structure with } R_1, R_2, R_3, R_4, X$$

wherein $R_1$ is selected from the group consisting of the formula (II), (III) and (IV):

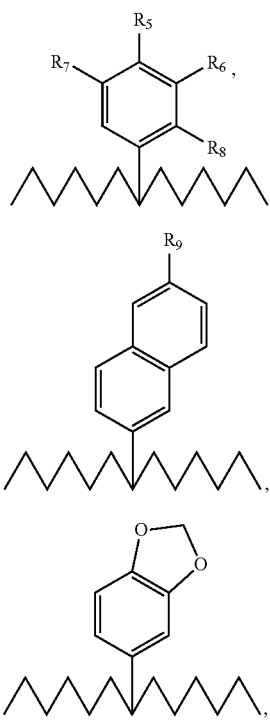

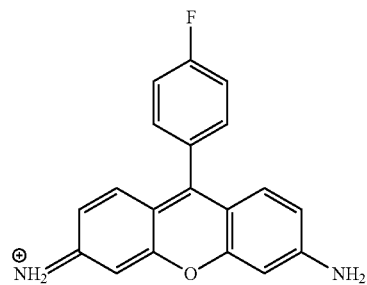

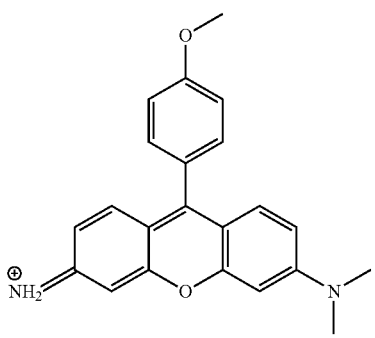

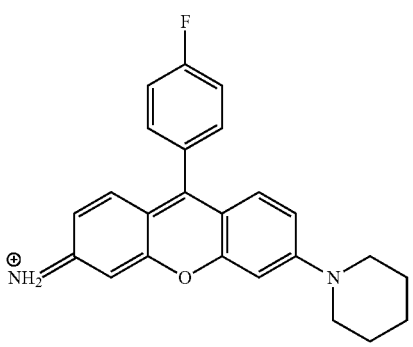

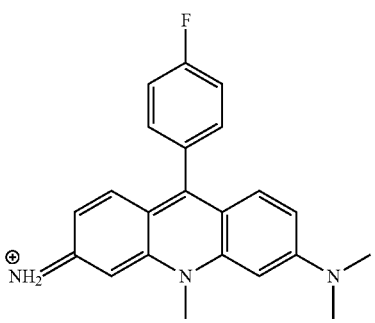

wherein $R_5$, $R_6$, $R_7$, $R_8$ and $R_9$ are respectively selected from the group consisting of hydrogen, halogen, C1 to C6 alkyl, phenyl, —$OR_{10}$ and —$SR_{10}$, wherein $R_{10}$ is C1 to C6 alkyl or aryl, wherein $R_2$, $R_3$ and $R_4$ are respectively selected from the group consisting of hydrogen, C1 to C6 alkyl and —$(CH2)_{bill}NR_{11}R_{12}$, and m is an integer of 1 to 12; and $R_{11}$ and $R_{12}$ are respectively selected from the group consisting of hydrogen, C1 to C6 alkyl and chloroacetyl, or $R_2$, and $R_3$ form the cyclic conformation of the formula (V) together with the nitrogen atom to which R, and R3 are bound:

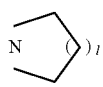

wherein 1 is an integer of 1 to 6, and X is selected from the group consisting of O, S, NH and $NR_{13}$, wherein $R_{13}$ is C1 to C6 alky; and wherein the sample cells which have accumulated the compound are the non-differentiated pluripotent cells (ii) detecting the non-differentiated pluripotent cells.

8. The method of claim 1, wherein:
$R_2$ and $R_3$ are respectively selected from the group consisting of hydrogen, methyl, ethyl, dimethylaminoethyl and 10-chloroacethylaminodecyl or $R_2$ and $R_3$ form the cyclic conformation of 1-piperidinyl;
$R_4$ is methyl;
$R_5$ is selected from the group consisting of hydrogen, fluorine, methoxy, phenoxy, methylthio, methyl, propyl and phenyl;
$R_6$ and $R_7$ are respectively selected from the group consisting of hydrogen, fluorine, chlorine, methoxy and methyl;
$R_8$ is fluorine;
$R_9$ is methoxy; and
X is selected from the group consisting of O, S and methylamino.

9. The method of claim 8, wherein the compound is selected from the group consisting of the compounds shown in Table 1 below:

TABLE 1

TABLE 1-continued
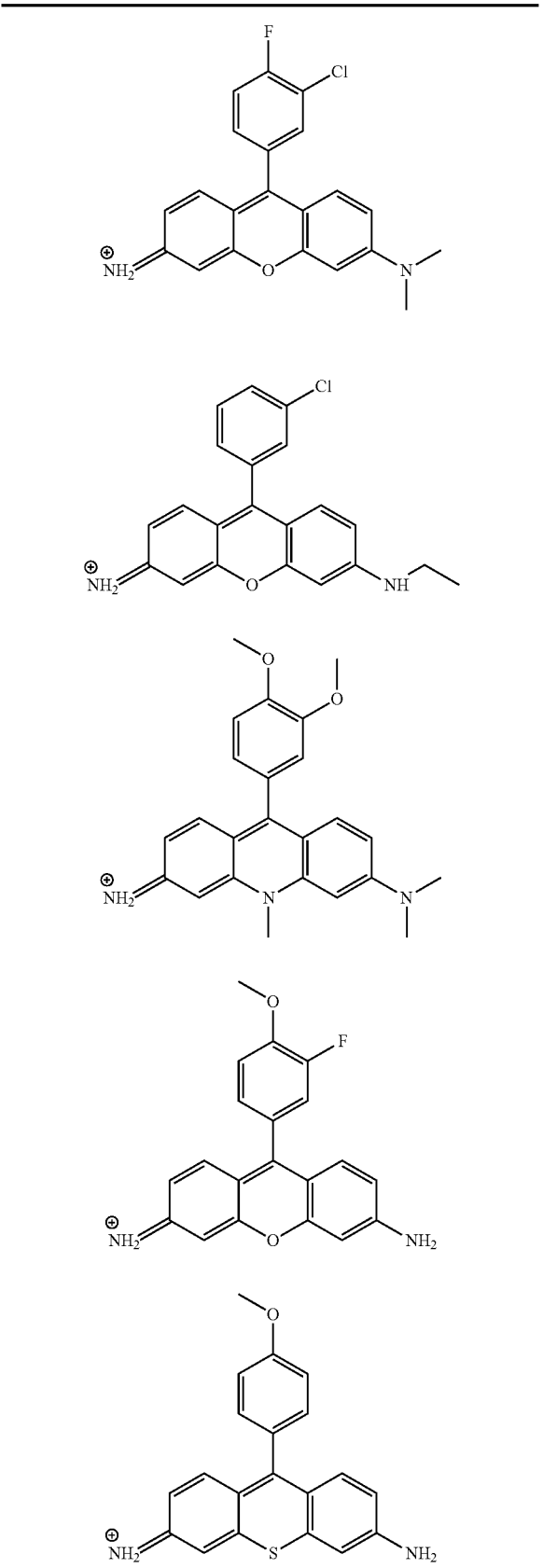
TABLE 1-continued
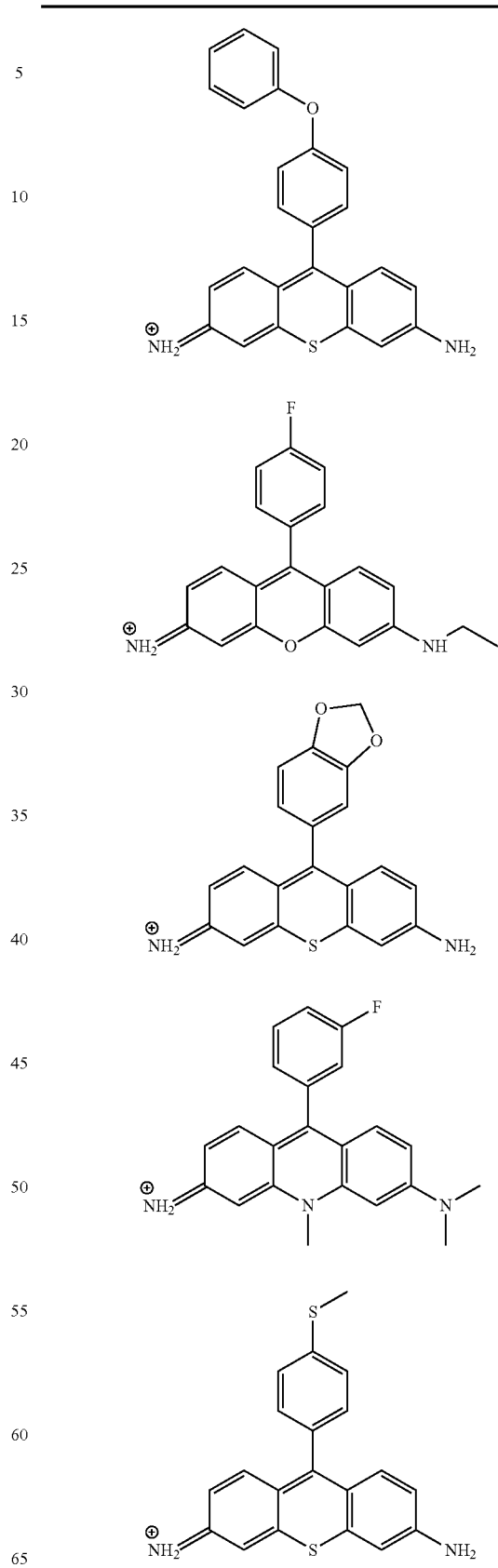

TABLE 1-continued
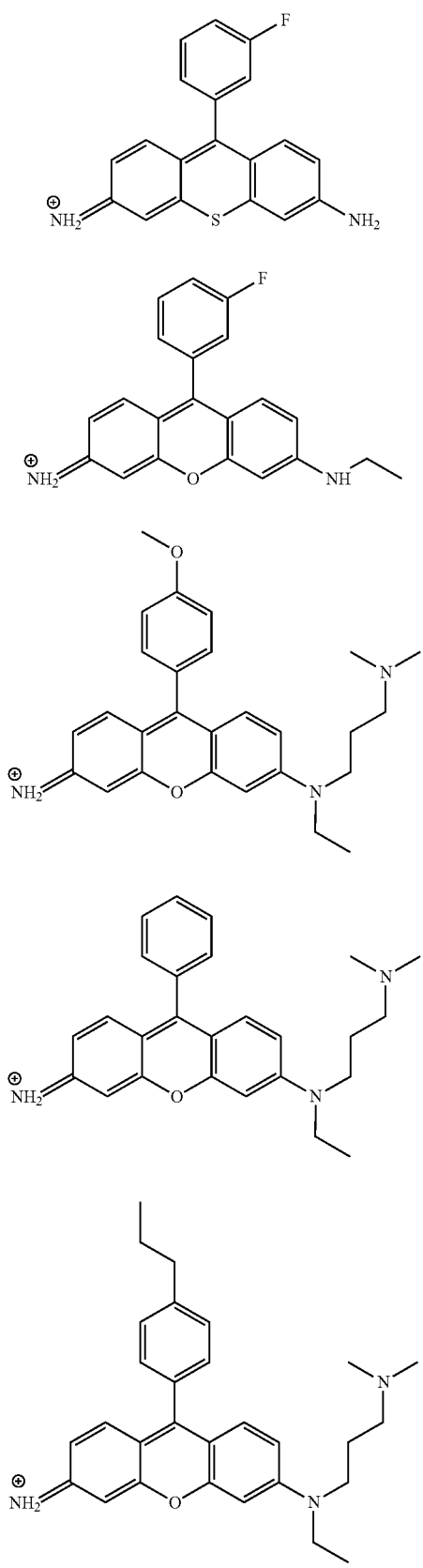
TABLE 1-continued
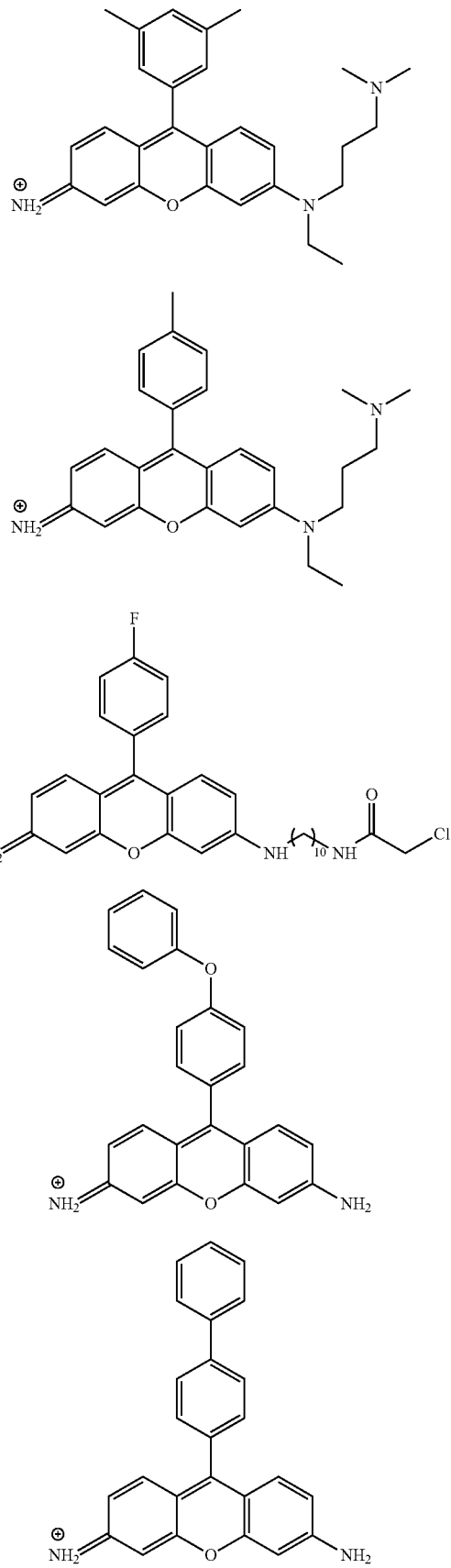

TABLE 1-continued
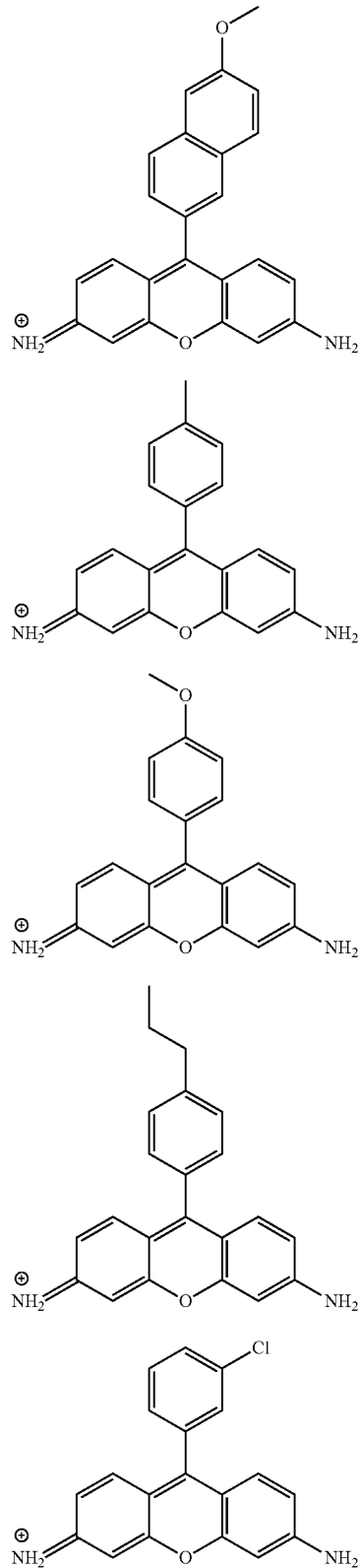
TABLE 1-continued
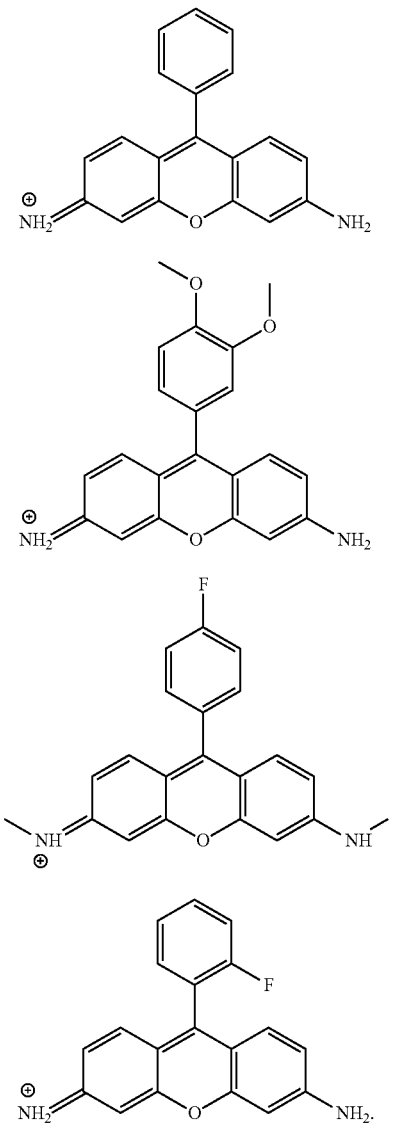
10. The method of claim 9, wherein the compound has the following formula
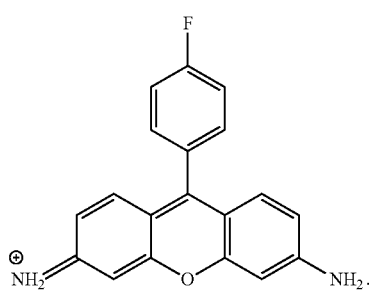 [SMILES: Nc1ccc2c(-c3ccc(F)cc3)c3ccc(=[NH2+])cc-3oc2c1]
* * * * *